(12) United States Patent
Barak

(10) Patent No.: US 11,427,482 B2
(45) Date of Patent: Aug. 30, 2022

(54) SYSTEM AND METHOD FOR MONITORING PROCESS WATER TREATED WITH A BIOCIDE USING AN OXYGEN SENSOR

(71) Applicant: A.Y. LABORATORIES LTD., Tel Aviv (IL)

(72) Inventor: Ayala Barak, Tel Aviv (IL)

(73) Assignee: A.Y. LABORATORIES LTD., Tel Aviv (IL)

( * ) Notice: Subject to any disclaimer, the term of this patent is extended or adjusted under 35 U.S.C. 154(b) by 0 days.

(21) Appl. No.: 16/973,343

(22) PCT Filed: Jun. 3, 2019

(86) PCT No.: PCT/IL2019/050631
§ 371 (c)(1),
(2) Date: Dec. 8, 2020

(87) PCT Pub. No.: WO2019/239401
PCT Pub. Date: Dec. 19, 2019

(65) Prior Publication Data
US 2021/0253447 A1 Aug. 19, 2021

Related U.S. Application Data

(60) Provisional application No. 62/684,305, filed on Jun. 13, 2018.

(51) Int. Cl.
*C02F 1/00* (2006.01)
*A01N 59/00* (2006.01)
(Continued)

(52) U.S. Cl.
CPC .............. *C02F 1/008* (2013.01); *A01N 59/00* (2013.01); *C02F 1/76* (2013.01); *G01N 21/64* (2013.01);
(Continued)

(58) Field of Classification Search
None
See application file for complete search history.

(56) References Cited

U.S. PATENT DOCUMENTS

| 5,224,051 A | 6/1993 | Johnson |
| 6,132,628 A | 10/2000 | Barak |

(Continued)

FOREIGN PATENT DOCUMENTS

| CN | 101058450 | 10/2007 |
| CN | 103053613 | 4/2013 |
| CN | 104685063 | 6/2015 |

OTHER PUBLICATIONS

Applicant: A.Y Laboratories LTD; "System and Method for Monitoring Process Water Treated with a Biocide using an Oxygen Sensor"; European Application No. 19820153.5; European Office Action dated Feb. 25, 2022; 7 pgs.

(Continued)

*Primary Examiner* — Richard C Gurtowski
(74) *Attorney, Agent, or Firm* — Tarolli, Sundheim, Covell & Tummino LLP

(57) ABSTRACT

A system and method for monitoring process water treated with a biocide is provided. The system includes a biocide feeding unit and a dissolved oxygen sensor. The dissolved oxygen sensor works in two modes, a biocide feeding mode and a background mode, and alerts an operator when the dissolved oxygen value indicates a fault in the system. A drop in dissolved oxygen during feeding can indicate faulty production of biocide or biocide degradation, both of which can lead to unwanted disinfection by-products.

26 Claims, 12 Drawing Sheets

(51) Int. Cl.
  *C02F 1/76*   (2006.01)
  *G01N 21/64*  (2006.01)
  *G01N 33/18*  (2006.01)
  *C02F 103/02* (2006.01)
  *C02F 103/28* (2006.01)

(52) U.S. Cl.
  CPC ........ *G01N 33/18* (2013.01); *C02F 2103/023* (2013.01); *C02F 2103/28* (2013.01); *C02F 2209/003* (2013.01); *C02F 2209/008* (2013.01); *C02F 2209/22* (2013.01); *C02F 2303/08* (2013.01)

(56) References Cited

U.S. PATENT DOCUMENTS

| | | |
|---|---|---|
| 8,012,758 B2 | 9/2011 | Enzien et al. |
| 8,444,858 B2 | 5/2013 | Barak |
| 2005/0139530 A1* | 6/2005 | Heiss ............ C02F 9/00 210/85 |
| 2010/0078393 A1 | 4/2010 | Yin |
| 2014/0088190 A1 | 3/2014 | McNeel et al. |
| 2015/0014165 A1 | 1/2015 | Pressman et al. |
| 2015/0125347 A1* | 5/2015 | Machuca ........ G01N 21/643 422/82.07 |
| 2015/0203308 A1 | 7/2015 | Higaki |
| 2015/0351389 A1 | 12/2015 | Kolari et al. |
| 2015/0367315 A1 | 12/2015 | Barak |

OTHER PUBLICATIONS

Applicant: A.Y. Laboratories LTD; "System and Method for Monitoring Process Water Treated with a Biocide using an Oxygen Sensor"; European Application No. 19820153.5; Extended European Search Report dated Sep. 9, 2021; 9 pgs.

Official Action dated Jun. 21, 2022 which issued during the prosecution of Applicant's Chinese App No. 201980032787.0.

* cited by examiner

SYSTEM AND METHOD FOR MONITORING PROCESS WATER TREATED WITH A BIOCIDE USING AN OXYGEN SENSOR

CROSS-REFERENCE TO RELATED APPLICATIONS

The present invention is a U.S. National Stage under 35 USC 371 patent application, claiming priority to Serial No. PCT/IL2019/050631, filed on 3 Jun. 2019; which claims priority to U.S. 62/684,305, filed on 13 Jun. 2018 and entitled SYSTEM AND METHOD FOR MONITORING PROCESS WATER TREATED WITH A BIOCIDE USING AN OXYGEN SENSOR, the disclosures of which are is hereby incorporated by reference and priority of which is hereby claimed pursuant to 37 CFR 1.78.

Reference is made to U.S. patent application Ser. No. 07/892,533, filed Jun. 1, 1992 and entitled PROCESS AND COMPOSITIONS FOR THE DISINFECTION OF WATERS, U.S. patent application Ser. No. 08/809,346, filed Jan. 27, 1998 and entitled METHOD AND APPARATUS FOR TREATING LIQUIDS TO INHIBIT GROWTH OF LIVING ORGANISMS, U.S. patent application Ser. No. 10/586,349, filed Jul. 14, 2006 and entitled BIOCIDES AND APPARATUS, and U.S. patent application Ser. No. 14/765,335, filed Aug. 1, 2015 and entitled METHOD FOR CONTROLLING THE PRODUCTION OF A BIOCIDE, the disclosures of which are hereby incorporated by reference.

FIELD OF THE INVENTION

The present invention relates to a system and method for monitoring process water treated with a biocide using an oxygen sensor.

BACKGROUND OF THE INVENTION

Various techniques are known for monitoring process water.

SUMMARY OF THE INVENTION

The present invention seeks to provide a system and method for monitoring process water being treated by a biocide.

There is thus provided in accordance with a preferred embodiment of the present invention a system for feeding an oxidizing biocide to process water and monitoring the process water for potential degradation of the biocide thereby forming, as a result of such degradation, an active halogen compound, the system including: a biocide feeding conduit for feeding the biocide to the process water at a biocide inlet; and a degradation detection module including a dissolved oxygen sensor downstream of the biocide inlet.

In accordance with a preferred embodiment of the present invention, the process water is in a cooling tower. In accordance with an alternative preferred embodiment of the present invention, the process water is in a paper mill. The process water in the paper mill preferably contains starch. In accordance with a further preferred embodiment of the present invention, the process water is in a sugar production facility.

In accordance with a preferred embodiment of the present invention, the system further includes a biocide production system for producing the oxidizing biocide synchronously with the feeding. Preferably, the biocide production system produces the oxidizing biocide by mixing a hypochlorite oxidant and an ammonium salt. In a preferred embodiment, the ammonium salt is selected from ammonium carbamate, ammonium carbonate, ammonium bicarbonate, ammonium bromide, ammonium chloride, ammonium sulfate, ammonium sulfamate and ammonium hydroxide. Preferably, the ammonium salt is selected from ammonium carbamate, ammonium bromide and ammonium sulfate.

In accordance with a preferred embodiment of the present invention, the dissolved oxygen sensor is a luminescence based dissolved oxygen sensor. Preferably, the system further includes a controller that records measurements of the dissolved oxygen sensor. In accordance with a preferred embodiment of the present invention, the controller includes a display to display a warning based on the measurements of the dissolved oxygen sensor. Preferably, the controller includes a functionality for sending a warning to a remote location.

In accordance with a preferred embodiment of the present invention, the controller, when operating in a background mode, generates a baseline value for the dissolved oxygen level. Preferably, the controller raises a warning if the dissolved oxygen level deviates from the baseline value more than a preset threshold. In accordance with a preferred embodiment of the present invention, the controller, when operating in a feeding mode, raises a warning if there is a decrease in the dissolved oxygen level during feeding of the biocide or during an extended measurement period immediately following the feeding of the biocide. Preferably, the extended measurement period is 30 minutes, 20 minutes or 10 minutes.

In accordance with a preferred embodiment of the present invention, the controller is in communication with a biocide production system for producing the oxidizing biocide synchronously with the feeding. Preferably, the controller has functionality to control the biocide production system.

In accordance with a preferred embodiment of the present invention, the time for the process water to flow from the biocide inlet to the dissolved oxygen sensor is not more than 30 minutes, preferably not more than 20 minutes, more preferably not more than 10 minutes. In accordance with a preferred embodiment of the present invention, the active halogen compound is selected from the group consisting of $HOCl$, $HOBr$, $NHCl_2$ and $NH_2Br$. Preferably, the dissolved oxygen sensor is located in the flow of the process water.

There is also provided in accordance with another preferred embodiment of the present invention, in a process of feeding an oxidizing biocide to process water, a method for monitoring potential degradation of the biocide thereby forming, as a result of such degradation, an active halogen compound, the method including: providing a dissolved oxygen sensor in the process water downstream from a biocide inlet; and periodically measuring the level of dissolved oxygen in the process water.

In accordance with a preferred embodiment of the present invention, the process water is in a cooling tower. In accordance with a further preferred embodiment of the present invention, the process water is in a paper mill. Preferably, the process water in the paper mill contains starch. In accordance with an alternative preferred embodiment of the present invention, the process water is in a sugar production facility.

In accordance with a preferred embodiment of the present invention, the method further includes producing the oxidizing biocide synchronously with feeding the oxidizing biocide to the process water. Preferably, the producing includes producing the oxidizing biocide by mixing a hypochlorite oxidant and an ammonium salt. In accordance with a preferred embodiment of the present invention, the ammonium salt is selected from ammonium carbamate, ammonium carbonate, ammonium bicarbonate, ammonium bromide, ammonium chloride, ammonium sulfate, ammonium sulfamate and ammonium hydroxide. Preferably, the ammonium salt is selected from ammonium carbamate, ammonium bromide and ammonium sulfate.

In accordance with a preferred embodiment of the present invention, the dissolved oxygen sensor is a luminescence based dissolved oxygen sensor. Preferably, the method further includes communicating the level of dissolved oxygen to a controller. In accordance with a preferred embodiment of the present invention, the controller includes a display to display a warning based on the measurements of the dissolved oxygen sensor. Preferably, the controller includes a functionality for sending a warning to a remote location.

In accordance with a preferred embodiment of the present invention, the controller, when operating in a background mode, generates a baseline value for the dissolved oxygen level. Preferably, the controller raises a warning if the dissolved oxygen level deviates from the baseline value more than a preset threshold. In accordance with a preferred embodiment of the present invention, the controller, when operating in a feeding mode, raises a warning if there is a decrease in the dissolved oxygen level during the feeding or during an extended measurement period following the feeding. Preferably, the extended measurement period is 30 minutes, 20 minutes or 10 minutes.

In accordance with a preferred embodiment of the present invention, the controller is in communication with a biocide production system for producing the oxidizing biocide synchronously with the feeding. Preferably, the controller has functionality to control the biocide production system.

In accordance with a preferred embodiment of the present invention, the time for the process water to flow from the biocide inlet to the dissolved oxygen sensor is not more than 30 minutes, preferably not more than 20 minutes, most preferably not more than 10 minutes. In accordance with a preferred embodiment of the present invention, the active halogen compound is selected from the group consisting of HOCl, HOBr, $NHCl_2$ and $NH_2Br$. Preferably, the dissolved oxygen sensor is located in the flow of the process water.

BRIEF DESCRIPTION OF THE DRAWING

The present invention will be understood and appreciated more fully from the following detailed description, taken in conjunction with the drawings in which.

DETAILED DESCRIPTION OF THE INVENTION

Figure 1:
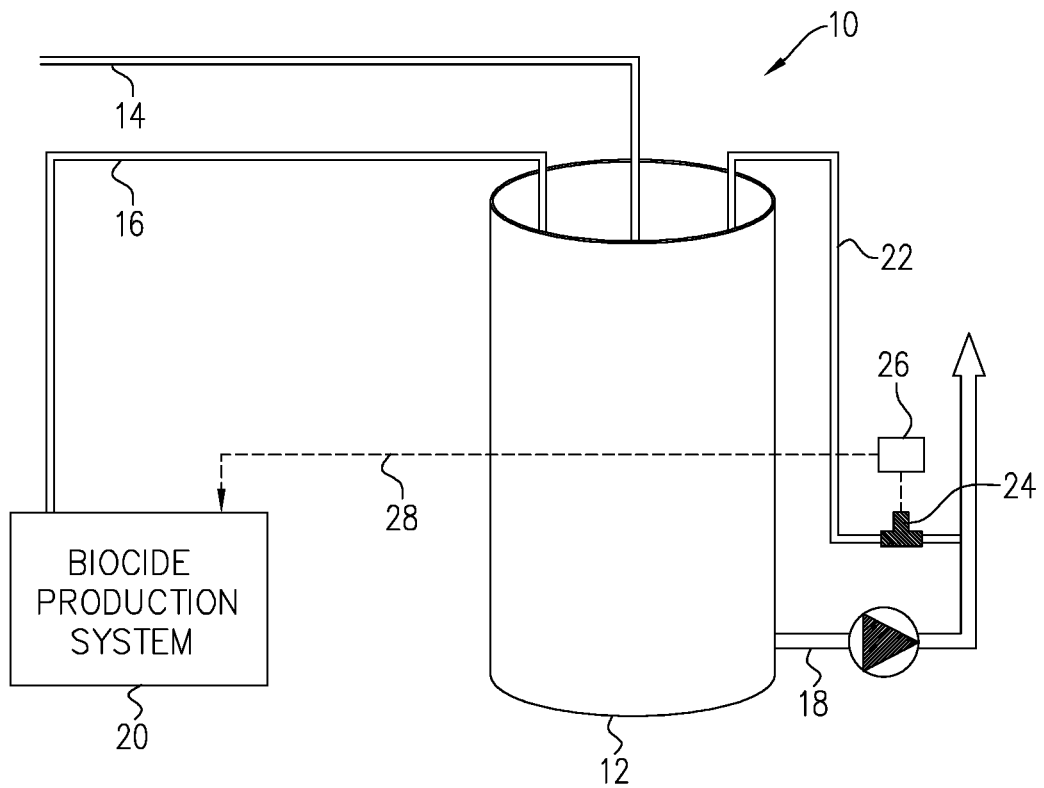
FIG. 1 is a simplified schematic of a system in accordance with one embodiment of the present invention.

As described in published European Patent Publication No. 0 517 102, the contents of which are incorporated herein by reference, biological fouling of circulating water is a well known problem caused by algae, fungi, bacteria, and other simple life forms found in circulating water. That patent publication describes controlling biofouling in high chlorine demand waters by mixing two components, one of which is an oxidant and the other an ammonium salt, and adding the mixture substantially immediately to the aqueous system to be treated. This produces the active biocidal ingredient, as described therein. A large number of examples of oxidants and ammonium salts are described in that patent publication.

A problem encountered in this method of treating liquid to inhibit growth of living organisms, however, is that the concentrated active biocidal ingredient is extremely non-stable chemically and quickly decomposes upon formation with the result that there is a fast drop in pH. This is especially so for active biocidal ingredients produced with no control. Therefore, when conventional dosing pumps and mixers are used in the absence of control the formed active biocidal ingredient quickly decomposes and loses its efficacy. Also, while the pH range of such concentrated active biocides is theoretically 10-12.5, the actual pH is lower and frequently unstable because of the fast decomposition. The biocide derived from ammonium bromide is particularly unstable, and thus more prone to degradation.

In U.S. Pat. No. 5,976,386, the contents of which are incorporated herein by reference, a method and apparatus for producing a biocide are disclosed that enable a constant ratio of oxidant/amine source to be maintained, thereby avoiding the need to use excess amine source in order to stabilize the reaction product and to maintain a reproducible product containing almost no degradation products. The novel method described therein includes producing an efficient in situ dilution of both the oxidant and the amine source and synchronously metering the two dilutions into a conduit to continuously mix therein according to a predetermined ratio to produce an active biocidal ingredient.

As already described in U.S. Pat. No. 5,976,386, careful control of the biocide formation is necessary. The biocide production process uses a multiple feeding point system requiring a separate control for each feed line since different pumps respond differently to pressure change, and pump feed rates depend on the water flow pressure. As for any on-site process, an online control is needed to ensure production of the right product at high yield, and with minimal side products. Furthermore, as shown in the above referenced patents, equimolar amounts of ammonium and hypochlorite are necessary for optimal performance. Excess hypochlorite, even local excess, leads to production of multi-chlorinated chloramines and degradation of the biocidal product monochloramine (MCA). With insufficient hypochlorite, the ammonium does not fully react, leading to a lower biocide concentration, excessive use of chemicals, higher cost of treatment, reduced efficacy, etc. The components used to make the biocide, such as sodium hypochlorite and ammonium carbamate, disclosed in U.S. Pat. No. 7,837,883, the contents of which are incorporated herein by reference, are unstable chemicals, and degrade with time during use.

There are known methods for ensuring the correct ratio between the feed of an ammonium salt and an oxidant. In U.S. Pat. No. 5,976,386 is disclosed the use of pH as an indicator of the end point of the reaction between an ammonium salt and sodium hypochlorite. Addition of hypochlorite to an ammonium salt solution increases the pH. However, after the equimolar point, the hypochlorite begins to degrade the biocidal MCA forming inorganic acids, which lower the pH. Thus, pH can be used as an indicator of the end point. U.S. Pat. No. 9,801,384, the contents of which are incorporated herein by reference, discloses the use of oxidation-reduction potential (ORP), conductivity, induction and oxygen saturation as parameters for indicating the ideal ratio between an ammonium salt and sodium hypochlorite.

In some cases, even if the biocide was optimally produced by the feeding unit, other parameters such as process water temperature, high local concentration of the produced biocide, process water pH and other water quality parameters can induce degradation of the biocide once it is mixed with the process water and potentially result in the production of unwanted disinfection by-products and consumption of process chemicals.

Monochloramines (MCA), such as those derived from a hypochlorite and an ammonium salt, are known to be inherently unstable (see, for example, Vikesland et al., "Effect of Natural Organic Matter on Monochloramine Decomposition: Pathway Elucidation through the Use of Mass and Redox Balances", *Environmental Science and Technology* 1998, 32(10):1409-1416; and Ozekin et al., "Modeling the Decomposition of Disinfecting Residuals of Chloramine", Water Disinfection and Natural Organic Matter, ACS Symposium Series 1996, pp. 115-125). The degradation of MCA in pure water is generally described by the following formula (1):

$$3NH_2Cl \rightarrow N_2 + NH_3 + 3HCl \tag{1}$$

The rate of this degradation depends, inter alia, on the initial molar ratio of Cl/N, the pH, temperature, and the concentration of MCA. In the presence of organic matter, monochloramine can react with the organic matter to form benign products.

However, under some conditions, monochloramine can degrade to form active halogen compounds, such as hypochlorous acid (HOCl) and dichloramine ($NHCl_2$), and in the presence of bromide such as when using ammonium bromide to form MCA, monobromamine ($NH_2Br$) and hypobromous acid (HOBr). $NHCl_2$ and $NH_2Br$ can also form the higher order substituted compounds $NCl_3$, $NHBr_2$ and $NBr_3$. These active halogens are less chemically stable than MCA, degrade much faster and are much more reactive. The active halogens derived from the degradation of MCA can lead to the production of undesired disinfection by-products. Halogenated disinfection by-products present a particular hazard due to their potential toxicity. The most familiar halogenated by-products are chloroform, bromoform, and chlorinated and brominated organic acids, but the halogenated by-products depend on the organic content of the water, and most of them have not been elucidated.

The analysis of disinfection by-products requires time-consuming laboratory procedures. In our previous patents and applications, we described the special attention needed in order to maintain continuous control of the process in order to ensure the production of MCA alone, and avoid degradation and presence of degradation intermediates in the biocide stock solution which is fed to process water. Feeding MCA to water with a high demand for chlorine will reduce the stability of the MCA compared to use of MCA in water with very low demand, and it is thus important to maximize the stability of the MCA and reduce avoidable fast degradation. A higher stability of the MCA in process water increases its biocidal efficiency, reduces chemical usage, and also reduces the production of disinfection by-products.

Monitoring process water is an essential step in evaluating treatment efficiency. The role of people in monitoring water quality is essential, but online monitoring is an essential tool in making human monitoring feasible. Minimizing the number of parameters to be monitored online is important because it reduces the handling and cost of online monitoring devices and makes it more feasible. Online monitoring enables feedback control, which is essential for immediate response for a problem. Online identification of fast degradation conditions, as well as feedback steps to reduce this degradation, are important for treatment optimization and environmental protection.

U.S. Pat. No. 8,012,758 discloses an apparatus for measuring microbiological activity using oxygen consumption rate. A sample is drawn from the process water and the dissolved oxygen concentration is measured upon sampling and after an amount of time. A decrease in the oxygen concentration is indicative of microbiological activity. U.S. Pat. No. 9,970,919 discloses a similar apparatus that measures oxygen concentration and/or rH. The sampling time in these apparatus is 0.5-2 hours. A similar method is disclosed in Standard Methods for the Examination of Water and Wastewater (1999), Method 2710B. Other systems involve a complete monitoring strategy monitoring corrosion and biofouling using a series of electrochemical probes as disclosed in On-Line Systems Aid Cooling System Chemistry Control (Schaefer and Pilsits, Industrial Waterworld 2003) and Cristiani and Perboni, "Antifouling strategies and corrosion control in cooling circuits", Bioelectrochemistry 2014, 97:120-126.

None of the above-mentioned systems discloses detecting degradation of a biocide. What is needed is a system with a simple, preferably online measurement that can identify a fault in the process water quickly that may be related to biocide degradation and alert the operator in real time to take corrective steps or to take corrective steps automatically. Oxygen is involved in many different processes that occur in industrial water. For example, oxygen is consumed by microbial activity and by corrosion processes. Oxygen is absorbed into water during cooling of water in an open cooling tower if cooling is efficient and in process water when water is in contact with air.

Measuring dissolved oxygen in process water during feeding of oxidizing biocides, strong oxidizers or weak oxidizers, has revealed a fast reduction in dissolved oxygen in many cases. A reduction in the level of dissolved oxygen as a result of biocide feeding is indicative of biocide degradation. Thus, dissolved oxygen can serve as a parameter for monitoring biocide degradation and the potential production of disinfection by-products in real time.

In accordance with a first embodiment of the present invention, there is provided a system for monitoring process water that is treated with a biocide for potential degradation of the biocide. The system comprises a biocide feeding system for feeding biocide to process water, a dissolved oxygen sensor and optionally one or more additional sensors.

The process water may be in any system having circulating or once through process water. In one embodiment, the process water may be part of a cooling system. In an alternative embodiment, the process water may be part of a paper production facility. In this embodiment, the process water preferably contains starch. In a further embodiment, the process water may be part of a food processing facility, such as for producing sugar or processing starch. In a still further embodiment, the process water may be part of a mining or oil drilling facility. In yet another embodiment, the process water may be part of a system for disinfection of fresh water or waste water.

The biocide feeding system can be any system that feeds a biocide to the process water. In one embodiment, the biocide feeding system comprises a pump that pumps a biocide produced off-site to the process water. Alternatively, the biocide feeding system may comprise a biocide production system for mixing two reactants to produce a biocide on-site and synchronously feed the biocide to the process water, such as the feeding systems disclosed in U.S. Pat. Nos. 5,976,386, 7,837,883 and 9,801,384. The biocide feeding system may feed biocide to the process water continuously or intermittently.

The biocide can be any suitable biocide. For example, the biocide can be an inorganic biocide such as chlorine dioxide ($ClO_2$), hypochlorous acid (HOCl), hypobromous acid (HOBr), or a chloramine derived from the mixing of a hypochlorite oxidant and an ammonium salt. In a preferred embodiment, the ammonium salt is selected from ammonium carbamate, ammonium carbonate, ammonium bicarbonate, ammonium bromide, ammonium chloride, ammonium sulfate, ammonium sulfamate and ammonium hydroxide (aqueous ammonia). More preferably, the ammonium salt is selected from ammonium carbamate, ammonium bromide and ammonium sulfate. In one embodiment, the ammonium salt is ammonium carbamate. In another embodiment, the ammonium salt is ammonium bromide. In a further embodiment, the ammonium salt is ammonium sulfate. The biocide can also be an organic biocide, such as glutaraldehyde, isothiazolinone derivatives including methylisothiazolone, methylchloroisothiazolinone and benzisothiazolinone, 2-bromo-2-nitropropane-1,3-diol (bronopol), 2,2-dibromo-2-cyanoacetamide (DBNPA) or a quaternary ammonium salt.

The dissolved oxygen sensor can be any available dissolved oxygen sensor. Preferably, the dissolved oxygen sensor is a luminescence-based dissolved oxygen sensor, wherein the presence of oxygen quenches the luminescence of an excited dye. For example, the dissolved oxygen sensor can be a luminescent dissolved oxygen sensor supplied by Hach Company (Loveland, Colo., USA), such as the LDO II sc electrode with an SC200 controller.

The one or more additional sensors can include a temperature sensor, a pH sensor, an oxidation-reduction potential (ORP) sensor, a conductivity sensor, an inductive conductivity sensor, a corrosion monitoring sensor for a specific metal, such as copper and different types of steel, biofilm monitoring devices, chemical fouling devices, turbidity monitoring devices and online instruments for measuring residual biocides such as free and total chlorine.

The dissolved oxygen sensor is placed in the process water. The dissolved oxygen sensor can be placed at any suitable location in the process water. Preferably, the dissolved oxygen sensor is placed at a location downstream from and close to the location of the biocide feeding point but at a sufficient distance to allow mixing of the biocide with the bulk process water. The average flow time of the process water from the biocide feeding point to the oxygen sensor is preferably not more than 30 minutes, more preferably not more than 20 minutes, and even more preferably not more than 10 minutes. The average flow time of the process water from the biocide feeding point to the oxygen sensor may be less than 1 minute, from 1 to 10 minutes, from 1 to 5 minutes, from 5 to 10 minutes, from 10 to 15 minutes, from 15 to 20 minutes, from 20 to 25 minutes or from 25 to 30 minutes. For example, in cooling water the dissolved oxygen sensor can be placed at or close to the outlet of the heat exchanges. In a paper mill, the oxygen sensor can be placed at or close to the outlet of the chest to which the biocide is fed. It can also be placed in chests where low pH additives such as aluminum salts or wet strength agents are fed.

The dissolved oxygen sensor operates in two different modes. In a background mode, the dissolved oxygen sensor measures the dissolved oxygen saturation at regular intervals. The time between measurements ranges from four minutes to 60 minutes, preferably from 10 minutes to 30 minutes. The measurements are recorded by a controller. The controller may be an integral part of the sensor, or may be located on an external device, such as a computer or portable communication device, in communication with the sensor. The controller may also be located in the biocide feeding unit or be in communication therewith.

The controller establishes a baseline value for the oxygen saturation. In the background mode, the baseline value may range from 0.1% to 100% or more, preferably from 5% to 100%. The dissolved oxygen level can be measured in ppm (mg/L) or in % saturation. If a measurement differs from the baseline value by more than a preset threshold, the controller raises a warning. The threshold may be a 0.1 to 50% change, preferably 0.5%-50%, more preferably a 1 to 10% change. The warning may be displayed on a display device viewed by an operator or may be transmitted to a remote recipient, such as via the internet or telephone.

The warning raised by the controller indicates a fault in the process water. A decrease or increase in oxygen saturation can be indicative of changes in microbial contamination, since microorganisms consume oxygen. A decrease in oxygen saturation can also be indicative of corrosion of metal, a process which consumes oxygen. A decrease in oxygen saturation can also be indicative of the introduction of reducing agents such as sulfite and sulfide into the process water. An increase in oxygen saturation can indicate improved microbial control or the introduction of oxidizing agents such as hydrogen peroxide into the process water. The warning provides a general indication that there is a fault in the process water which must be investigated and addressed.

When a biocide is about to be fed to the process water at a feeding point adjacent to the dissolved oxygen sensor, a controller in communication with the dissolved oxygen sensor is alerted and switches the dissolved oxygen sensor from the background mode to a feeding mode. The feeding mode may begin prior to the biocide feeding, such as ten minutes prior to biocide feeding, five minutes prior to biocide feeding or two minutes prior to biocide feeding. In the feeding mode, the dissolved oxygen sensor operates at a higher frequency than in the background mode. Typically, the dissolved oxygen level is measured in the feeding mode every 2 to 15 minutes. For example, the dissolved oxygen level is measured every two minutes, every five minutes, every ten minutes or every 15 minutes. The feeding mode may continue for an extended measurement period after the biocide feeding stops. The extended measurement period may be up to about 30 minutes, such as 30 minutes, 20 minutes or 10 minutes.

During biocide feeding and for a short period thereafter, the dissolved oxygen level is expected to be stable or increase slightly. However, if the biocide is degrading and forming stronger oxidizing intermediates, or if strong oxidizers are fed, thus increasing the potential for forming disinfection by-products, the dissolved oxygen level decreases during biocide feeding. Therefore, a decrease in dissolved oxygen during the biocide feeding is a definite sign of a problem and the controller raises a warning if the dissolved oxygen level drops during feeding or during the extended measurement period.

The drop in dissolved oxygen close to the biocide feeding point during biocide feeding can be caused by degradation of the biocide. The degradation may result from a biocide which was not produced properly or by local conditions in the process water which promote degradation of the biocide. Degradation of the biocide in the process water indicates a potential for production of unwanted disinfection by-products.

While the exact cause of the drop in dissolved oxygen and/or degradation of the biocide is not immediately known, it is likely that the cause is related to an excess amount of oxidizing biocide. Accordingly, a first measure to reduce damage to the process water while the exact source of the problem is being investigated is to lower the feed rate of the oxidizer. In one embodiment, lowering the feed rate of the oxidizer, such as a strong oxidizer, includes lowering the total feed rate of the biocide. This may be performed by an operator receiving the warning from the controller. Alternatively, the controller may also control the biocide feed and automatically reduce the feed rate of the biocide.

In an alternative embodiment, when the biocide is a monochloramine generated from a hypochlorite oxidant and an ammonium salt, lowering the feed rate of the oxidizer may include lowering the feed rate of the hypochlorite only or increasing the feed rate of the ammonium salt. In a biocide feeding system which does not have an internal control of the ratio of the hypochlorite to ammonium feed rates, changing a feed rate may include manual changing of the feed rate by an operator. Alternatively, the controller may also control the feed rates of the biocide feed and the ratio thereof. In some embodiments, the biocide feeding system includes an internal control of the ratio of the hypochlorite to ammonium feed rates. For example, the internal control may use a control parameter as described in U.S. Pat. No. 5,976,386 or 9,801,384. The system of the present invention can supersede the internal control of the biocide production system and control the ratio between two feed rates.

Following the period of time after the biocide feeding as described above, the controller changes the mode of operation of the dissolved oxygen sensor to the background mode.

FIG. 1 is a simplified schematic of a system 10 in accordance with one embodiment of the present invention. System 10 includes a chest 12 or tank having a process water inlet 14, a biocide feeding line 16, a mixing device (not shown) and a process water outlet 18. Biocide feeding line 16 supplies the biocide from a biocide production system 20. In an alternative embodiment (not shown), system 10 does not include a biocide production system, but rather biocide is produced off-site and fed to chest 12 via a pump. In chest 12, the biocide is mixed with the process water. While a chest is shown, the mixing can also take place in another fluid-containing element such as a pipe.

Process water outlet 18 includes a sidestream 22 which is circulated back into chest 12. An oxygen sensor 24 is placed in sidestream 22. Oxygen sensor 24 is in communication with a local controller 26. Local controller 26 may include a transmitter that transmits data and/or instructions 28 to a controller of biocide production system 20. Instructions 28 may include instructions to increase or decrease the feed rate of the biocide. In an embodiment wherein the biocide is produced by mixing a hypochlorite oxidant with an ammonium salt, instructions 28 may include instructions to change the ratio between the oxidant and the ammonium salt.

Figure 2:
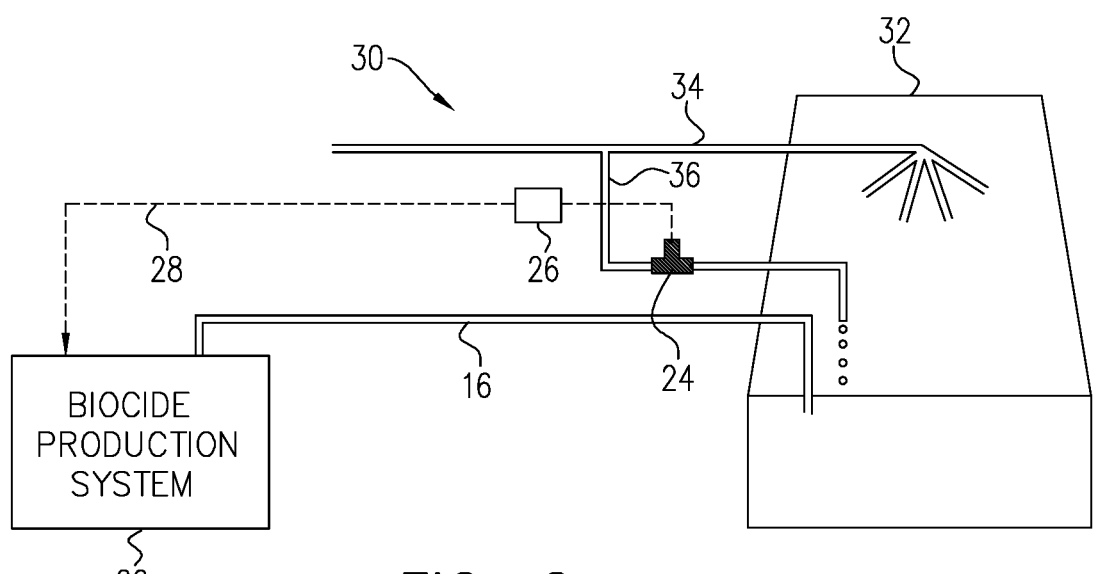
FIG. 2 is a simplified schematic of a system in accordance with another embodiment of the present invention.

FIG. 2 is a simplified schematic of a system 30 in accordance with another embodiment of the present invention. System 30 includes a cooling tower 32 having a cool water inlet (not shown), a biocide feeding line 16 and a warm water outlet 34. Biocide feeding line 16 supplies the biocide from a biocide production system 20 to the cool water entering cooling tower 32. In an alternative embodiment (not shown), system 30 does not include a biocide production system, but rather biocide is produced off-site and fed to cooling tower 32 via a pump.

Warm water outlet 34 has a sidestream 36 containing an oxygen sensor 24. Oxygen sensor 24 is in communication with a local controller 26. Local controller 26 may include a transmitter that transmits data and/or instructions 28 to biocide production system 20. Instructions 28 may include instructions to increase or decrease the feed rate of the biocide. In an embodiment wherein the biocide is produced by mixing a hypochlorite oxidant with an ammonium salt, instructions 28 may include instructions to change the ratio between the hypochlorite and the ammonium salt.

While FIGS. 1 and 2 show systems with one biocide inlet and one dissolved oxygen sensor, the system of the present invention may include multiple dissolved oxygen sensors, each one in proximity to and downstream from one of a plurality of biocide inlets. Each dissolved oxygen sensor is in communication with a controller and the corresponding biocide feeding is controlled based on the measurements of the dissolved oxygen sensor as described herein.

There is also provided in accordance with an aspect of the present invention a method for monitoring the state of process water that is treated with a biocide for potential degradation of the biocide, the method comprising: providing a dissolved oxygen sensor in the process water and periodically measuring the level of dissolved oxygen in the process water. The method may also comprise communicating the level of dissolved oxygen to a controller and raising a warning by the controller if the level of dissolved oxygen strays from an expected value.

The process water, biocide and dissolved oxygen sensor of the method are as described above with respect to the system of the invention. Periodically measuring the level of dissolved oxygen may include measuring the dissolved oxygen level every two minutes to every 60 minutes.

Raising a warning by the controller if the level of dissolved oxygen strays from an expected value is carried out in two modes. In a background mode, the dissolved oxygen sensor monitors the process water when a biocide is not being fed. In this mode, the dissolved oxygen is measured every 4 to 60 minutes, preferably every 10 to 30 minutes. The controller establishes a baseline value for the oxygen saturation. In the background mode, the baseline value may range from 0.1% to 100% or more, preferably from 0.5% to 100. If a measurement differs from the baseline value by more than a preset threshold the controller raises a warning. The threshold may be a 0.1 to 50% change, preferably 0.5%-50%, more preferably a 1 to 10% change. The warning may be displayed on a display device viewed by an operator or may be transmitted to a remote recipient, such as via the internet or telephone. The warning provides a general indication that there is a fault in the process water which must be investigated and addressed.

When a biocide is about to be fed to the process water the controller is alerted and switches the dissolved oxygen sensor from the background mode to a feeding mode. In the feeding mode, the dissolved oxygen level is measured every 2 to 15 minutes. For example, the dissolved oxygen level is measured every two minutes, every five minutes, every ten minutes or every 15 minutes. During the feeding of the biocide to the process water, there is an expected increase in dissolved oxygen due to the decrease in oxygen-consuming microorganisms. Therefore, in the feeding mode, the controller does not sound a warning due to an increase in dissolved oxygen. However, a decrease in dissolved oxygen during the feeding is a definite sign of a problem and the controller raises a warning if the dissolved oxygen level drops during feeding. The feeding mode may begin prior to the biocide feeding, such as up to ten minutes prior to biocide feeding, and continue for an extended measurement period after the biocide feeding, such as up to 30 minutes after biocide feeding stops.

EXAMPLES

Example 1

Figure 3:
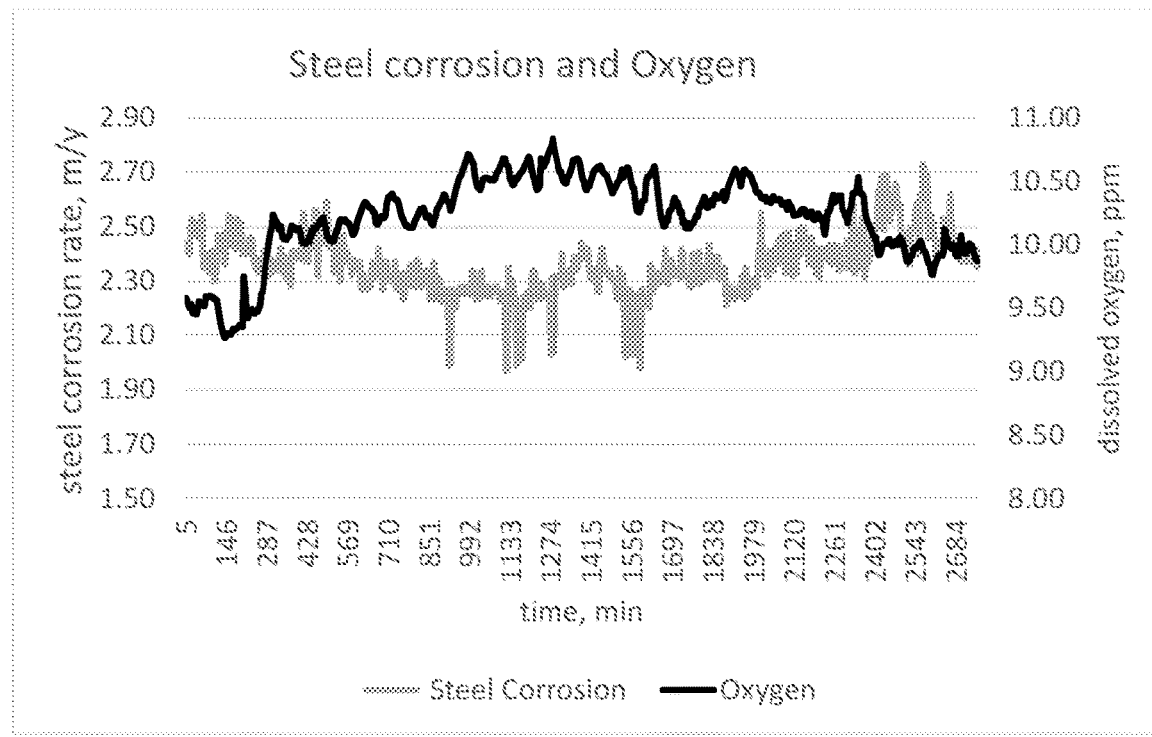
FIG. 3 is a graph showing the level of dissolved oxygen and the rate of steel corrosion in process water as a function of time.

A cooling tower is monitored by an elaborate electrochemical device to measure the corrosion rate of steel. In parallel, a simple oxygen electrode was installed. FIG. 3 shows that as the steel corrosion rate decreases, the dissolved oxygen concentration increases, and as the steel corrosion rate increases, the dissolved oxygen concentration decreases.

Figure 4:
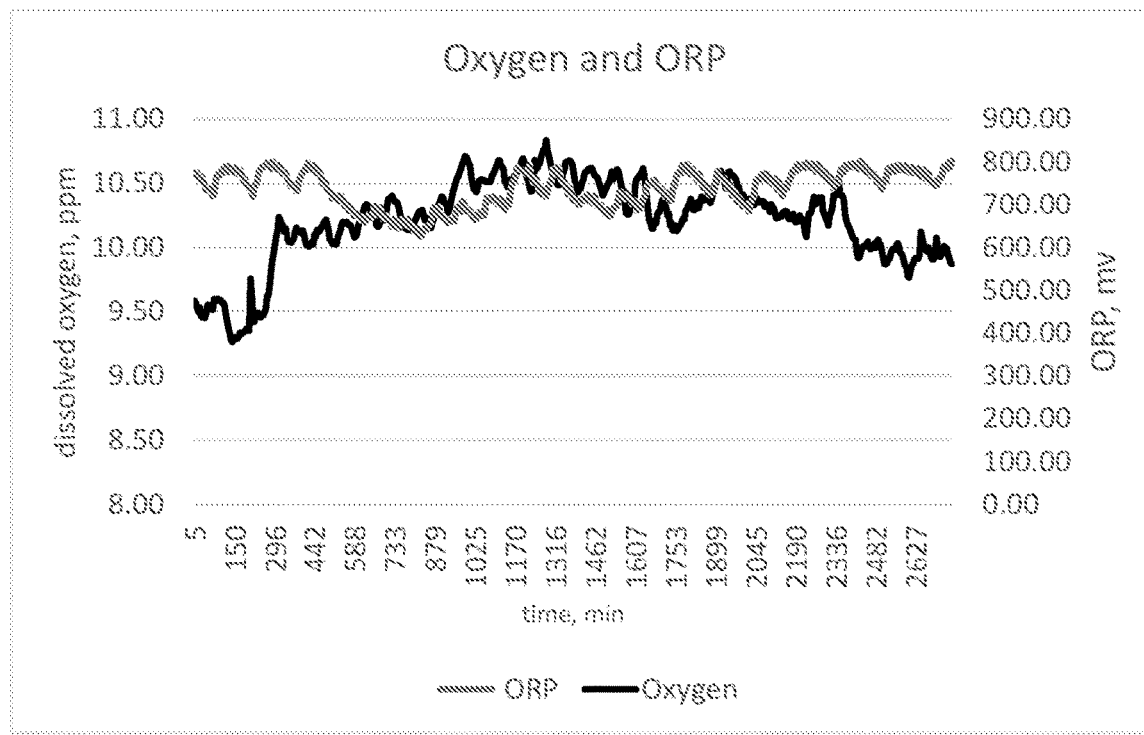
FIG. 4 is a graph showing the level of dissolved oxygen and the oxidation-reduction potential in process water as a function of time.

An ORP electrode was also installed and the results are shown in FIG. 4 together with the dissolved oxygen results. It can be seen that the ORP maintained a steady value throughout the sampling period and could not indicate that corrosion was taking place. On the other hand, the dissolved oxygen measurements did reflect the corrosion in the cooling system. This shows that dissolved oxygen can be used as an indicator of possible corrosion.

Example 2

Figure 5:
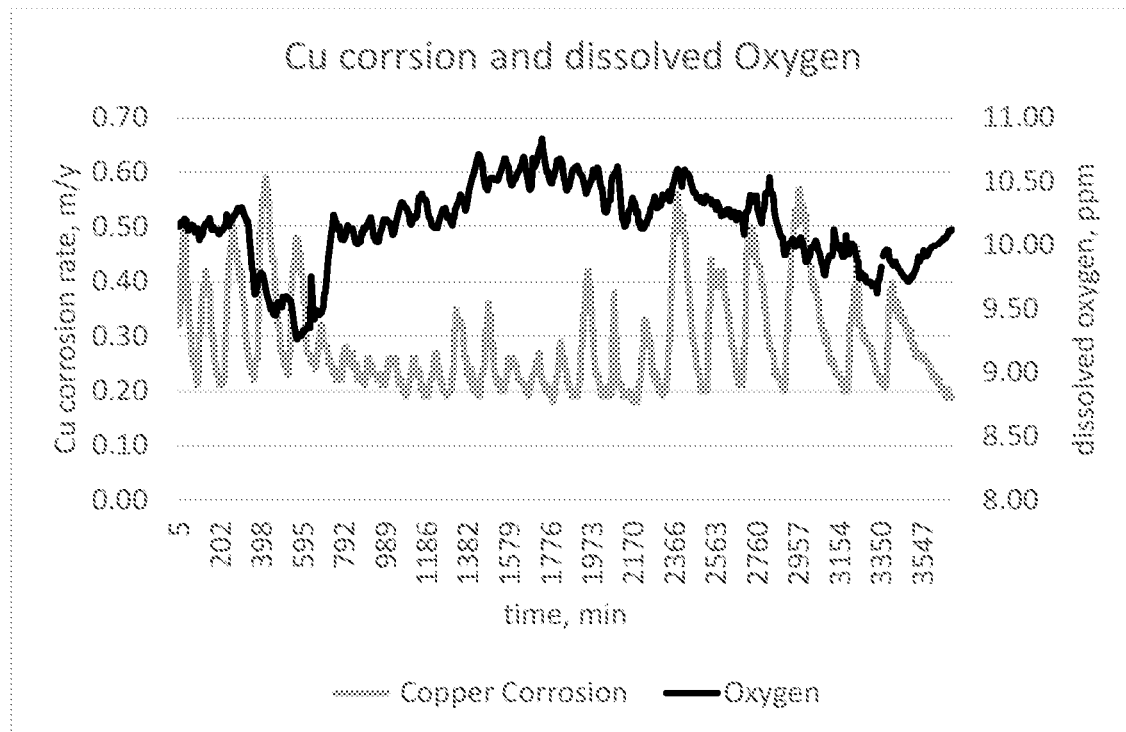
FIG. 5 is a graph showing the level of dissolved oxygen and the rate of copper corrosion in process water as a function of time.

Cooling water in a cooling tower was treated with hypobromous acid, a strong oxidizing biocide, and tolyltriazole, a copper corrosion inhibitor. ORP measured values were high indicating the presence of the strong oxidizer. The copper corrosion rate was measured using an elaborate electrochemical device as in the previous example. An oxygen sensor was also added, and the results are shown in FIG. 5.

The results show that the strong oxidizer reacts with the corrosion inhibitor, and as strong oxidizer is fed to the system the corrosion increases because the corrosion inhibitor is consumed when it reacts with the strong oxidizer. The reaction with the strong oxidizer consumes oxygen, and dissolved oxygen decreases in parallel to the consumption of the corrosion inhibitor. When the cooling water is saturated with oxygen passing through the cooling tower, the level of oxygen increases again. Oxygen drops again when the strong oxidizer is fed again and reacts with the corrosion inhibitor. This reaction between the strong oxidizer and the organic corrosion inhibitor results in the production of disinfection by-products. This example shows that the dissolved oxygen electrode can detect this reaction and serve as an indicator for potential production of disinfection by products.

Example 3

Figure 6:
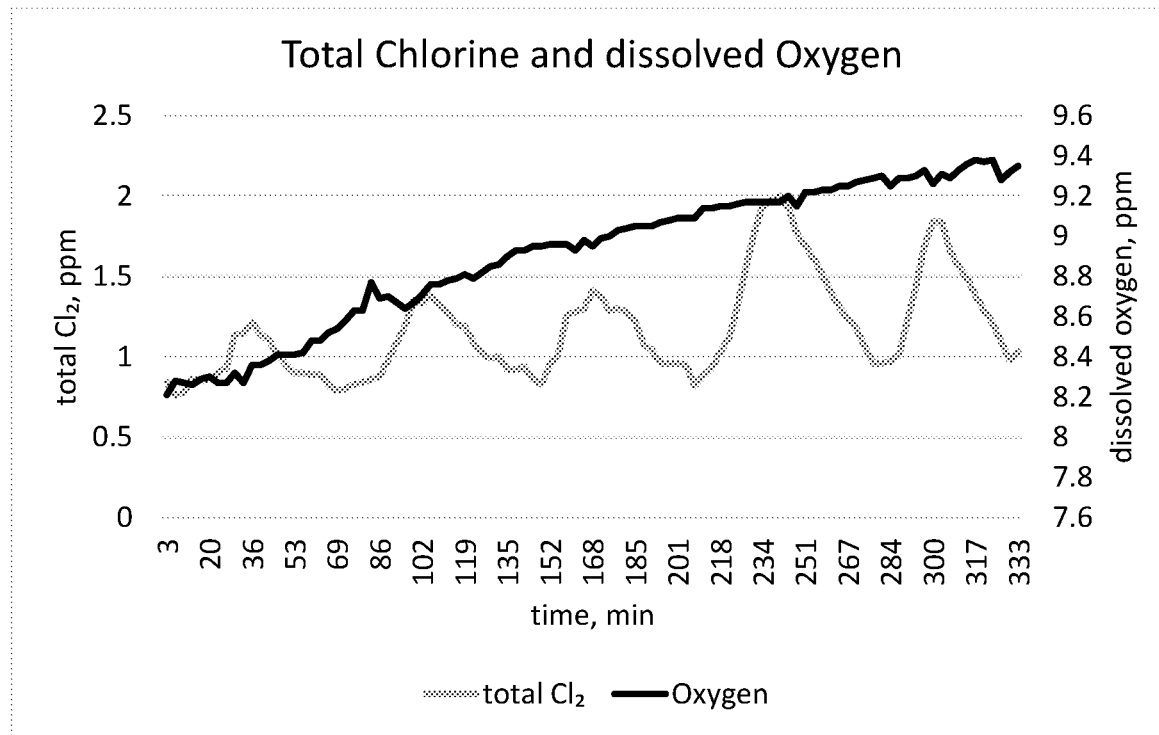
FIG. 6 is a graph showing the level of dissolved oxygen and the level of total chlorine in process water as a function of time.
Figure 7:
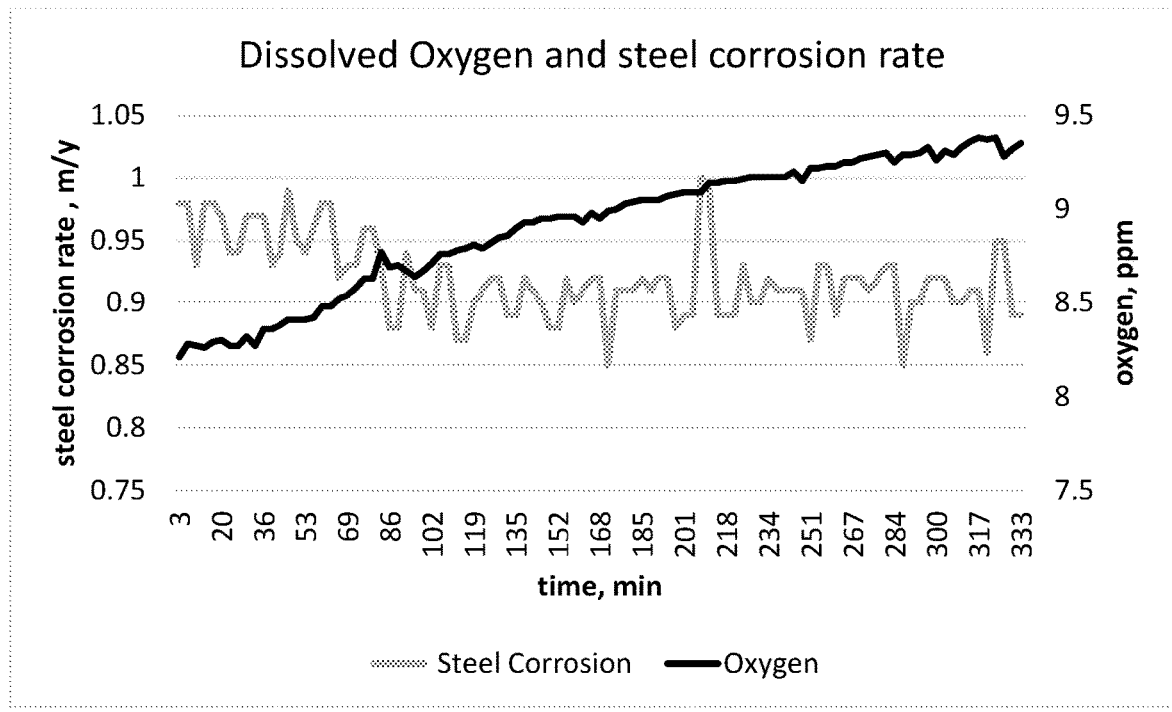
FIG. 7 is a graph showing the level of dissolved oxygen and the rate of steel corrosion in process water as a function of time.

Cooling water is treated with a monochloramine biocide generated from ammonium carbamate and sodium hypochlorite. Residual monochloramine (as total chlorine) and dissolved oxygen were measured as the biocide was intermittently dosed. FIG. 6 shows effective microbial control indicated by a steady increase in dissolved oxygen. The biocide is sufficient to control oxygen-consuming microorganisms and does not degrade or react with organic material present in the cooling water. The steel corrosion rate was measured and was shown to steadily decrease as dissolved oxygen increased as shown in FIG. 7. This shows that dissolved oxygen can serve as an indicator for corrosion control.

Example 4

Figure 8:
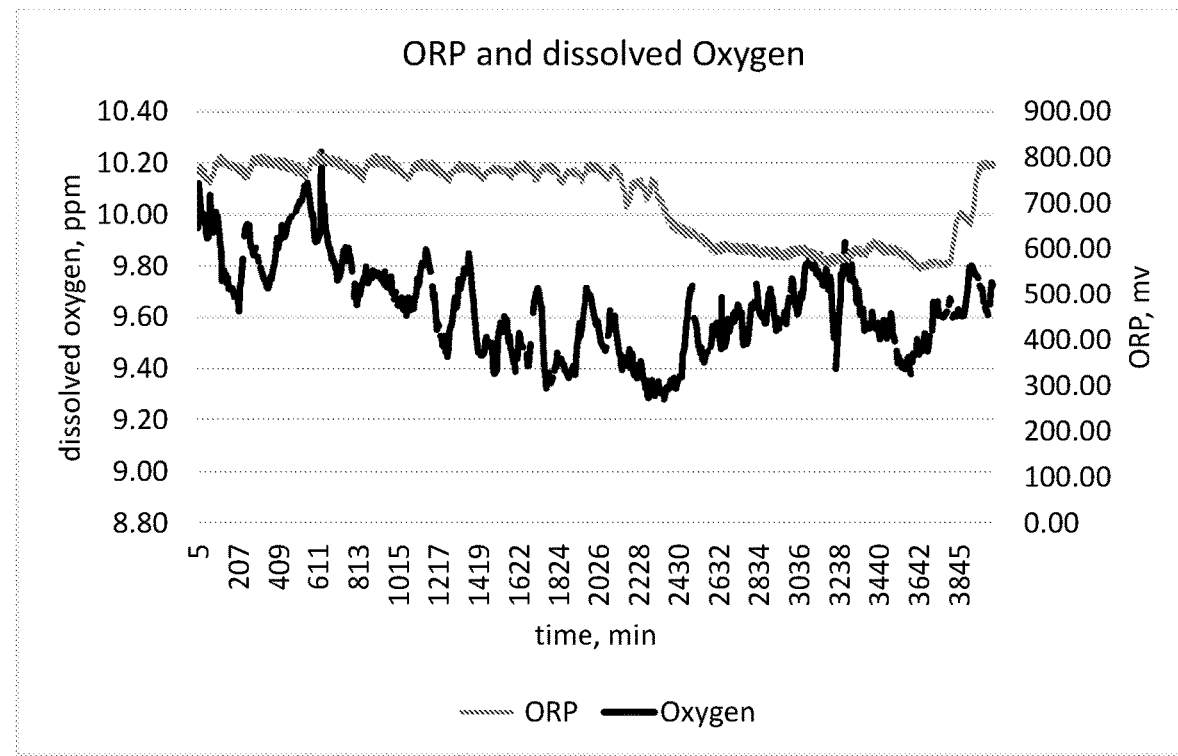
FIG. 8 is a graph showing the level of dissolved oxygen and the oxidation-reduction potential in process water as a function of time.

Cooling water from a cooling tower was treated with a strong oxidizing biocide, sodium bromide mixed with sodium hypochlorite. A steady increase in conductivity from 1600 to 2300 μS/cm was noted, due to an increase in concentration cycles initiated by the plant. With the increase in conductivity there is a parallel increase in concentration of any chemicals present in the cooling water, and the viable count of microorganisms is expected to increase. The water was monitored using both dissolved oxygen and ORP sensors. Dissolved oxygen is expected to drop due to increased oxygen consumption by the microorganisms, and the ORP is also expected to drop due to an increase in concentration of reducing compounds produced by the microorganisms. As can be seen in FIG. 8, the decrease in dissolved oxygen was observed well before the decrease in ORP. Dissolved oxygen is therefore a more sensitive marker for increased microbial activity than ORP. A controller detecting the decrease in dissolved oxygen that does not occur during biocide feeding can react to the problem by increasing the biocide feed rate to compensate for the increased microbial activity.

Example 5

Bromine-activated chloramine (BAC), a biocide produced by on-site mixing of ammonium bromide and sodium hypochlorite was fed to the mixing chest of a paper machine producing fine paper. BAC was fed every 180 minutes for 15 minutes. Dissolved oxygen, pH, and residual total chlorine (measured using N,N-diethyl-p-phenylenediamine (DPD)) were measured in the mixing chest (MC) and in the head box (HB) during BAC feeding and during feeding off-times. The average time for the process water to flow from the mixing chest to the head box is less than five minutes. Aerobic viable counts (MB) were measured in the head box samples. The measurements were conducted manually, on-site, as soon as samples were taken.

Figure 9:
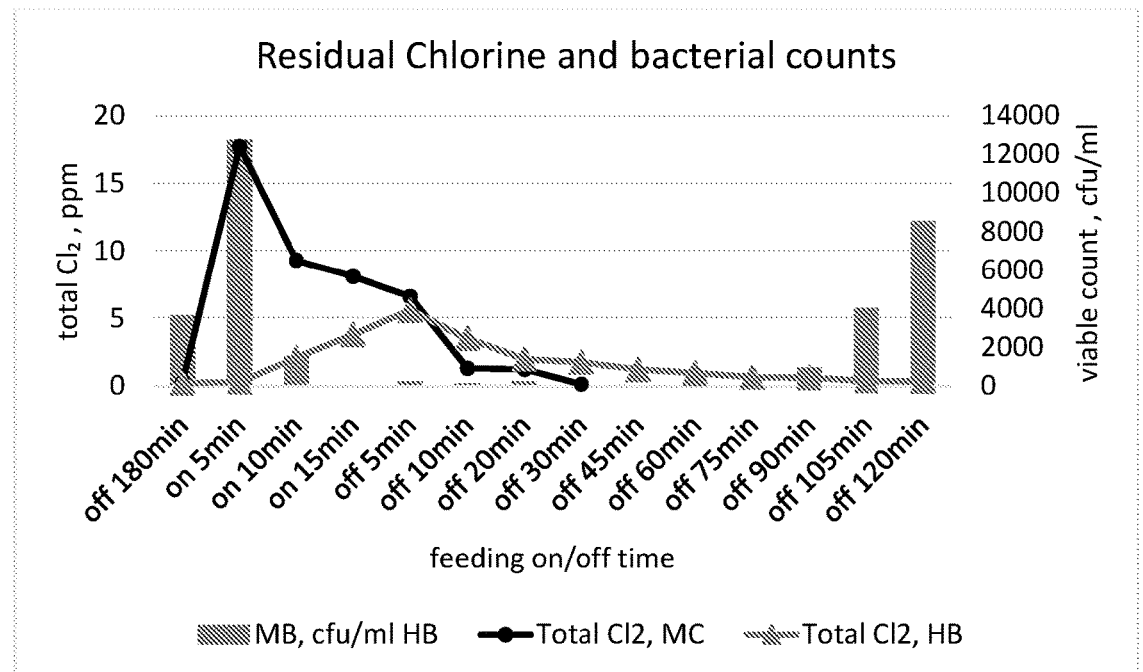
FIG. 9 is a graph showing the level of total chlorine and the bacteria count in process water as a function of time.

The expected results would be that the residual total chlorine in the MC would rise steadily during the feeding and would be maintained for about 5 minutes after the feeding stops. As shown in FIG. 9, the HB shows some residual after 10 minutes of feeding to the MC and the residual increases to a maximum of 5.6 ppm at 5 minutes off feeding, when the residual total chlorine in the MC is 6.6 ppm. The viable count decreases significantly as soon as residual is measured in the HB, and the count remains below detection limit and starts to increase after 90 minutes of off feeding. Both in the MC and in the HB the highest residual measured does not last for 15 minutes.

Figure 10:
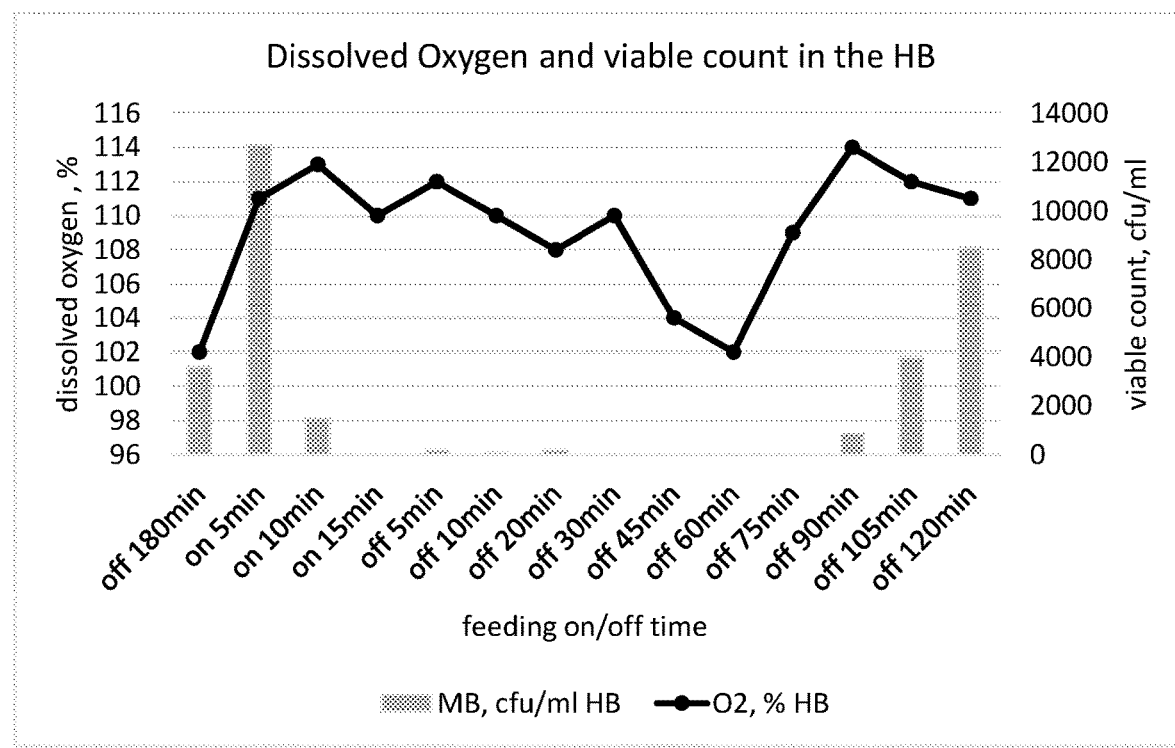
FIG. 10 is a graph showing the level of dissolved oxygen and the bacteria count in process water as a function of time.

FIG. 10 shows that the oxygen in the HB increases at 10 min on, when residual total chlorine from the MC first reaches the HB, and a significant drop in viable count is noted. However, contrary to the expectation that the oxygen will increase further, or at least remain at the same level, oxygen drops continuously during the following 50 minutes until 60 minutes off feeding where dissolved oxygen starts to increase in parallel to an increase in viable count. When viable counts increase further, oxygen starts to drop.

Figure 11:
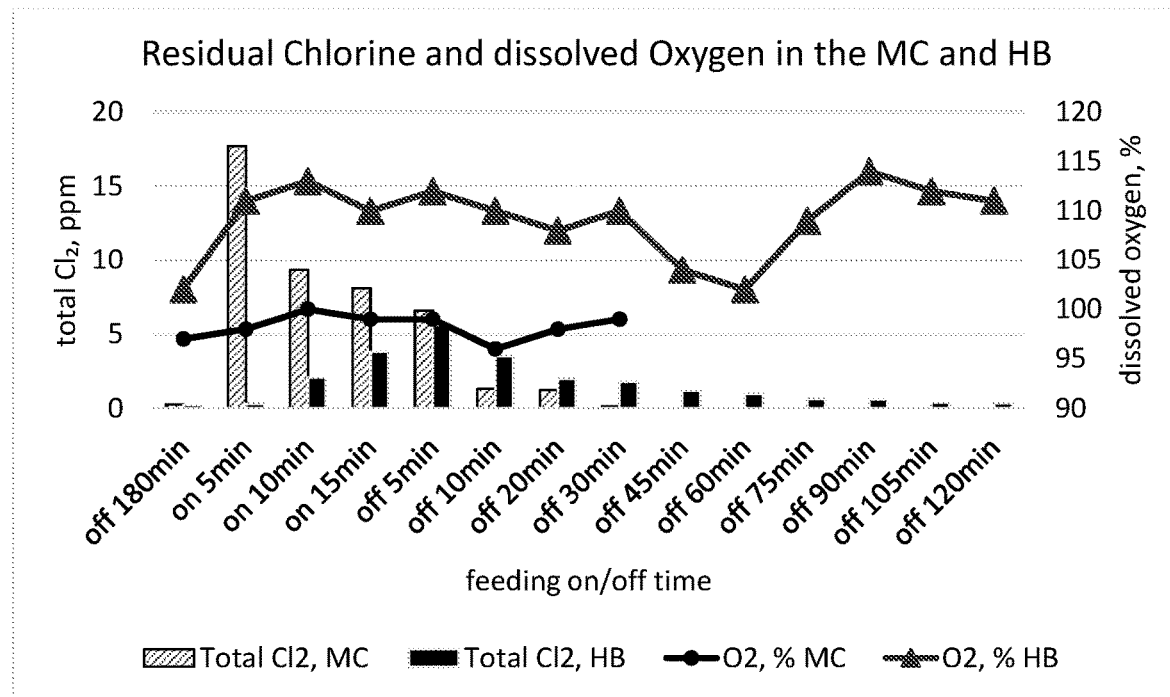
FIG. 11 is a graph showing the levels of dissolved oxygen and total chlorine in process water as a function of time.

FIG. 11 shows that both residual total chlorine and dissolved oxygen began to decrease during the feeding in both the MC and the HB. This is indicative of degradation of the biocide. Measuring residual total chlorine online is possible, but residual chlorine alone will not yield the same information, since fluctuations in residual chlorine are natural, and are not necessarily related to biocide degradation.

Figure 12:
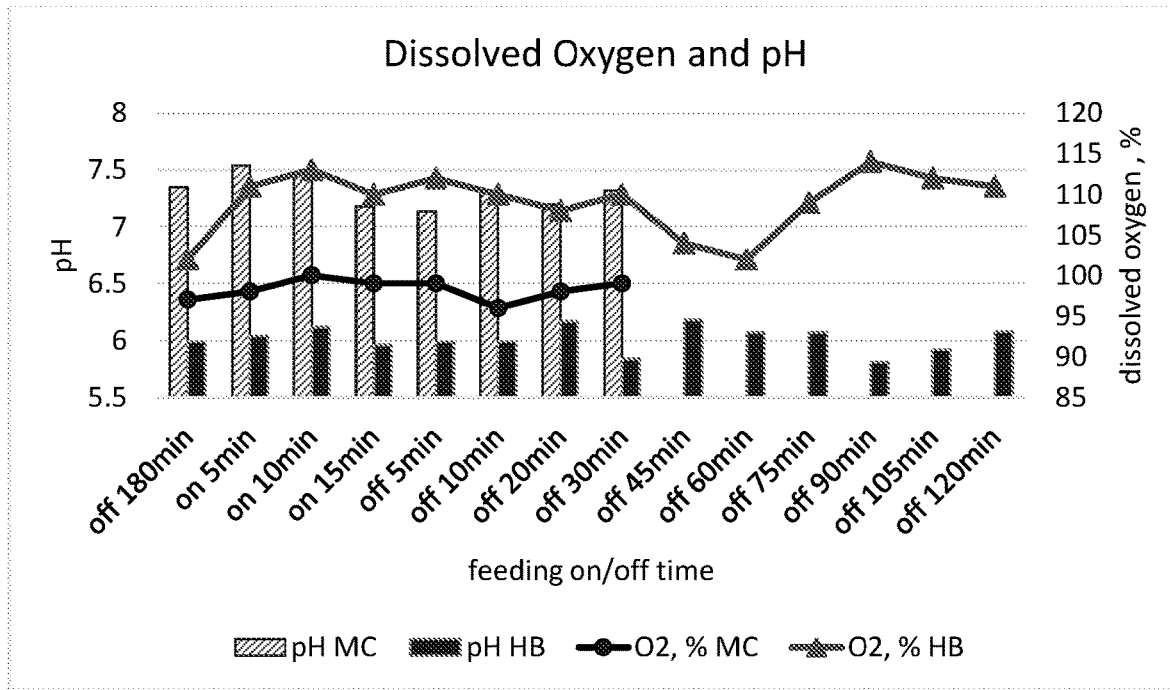
FIG. 12 is a graph showing the level of dissolved oxygen and the pH in process water as a function of time.

FIG. 12 shows that the pH in the MC is dropping while the oxygen decreases and the biocide degrades. The degradation and drop in dissolved oxygen is more pronounced in the HB because of the low HB pH. The low pH promotes degradation of BAC, and the degradation reduces the pH, leading to increased reduction in dissolved oxygen. Oxygen starts to increase when residual $Cl_2$ is too low to show any side reactions (0.65 ppm). Monitoring of dissolved oxygen manually or online during biocide feeding is a simple method to detect biocide loss due to degradation during feeding. The drop in dissolved oxygen due to faulty production of the biocide or due to specific conditions occurring in the process water upon feeding the biocide which promote BAC degradation is observable even when the background level of dissolved oxygen is low due to microbial contamination or high when the process water is effectively controlled.

Figure 13:
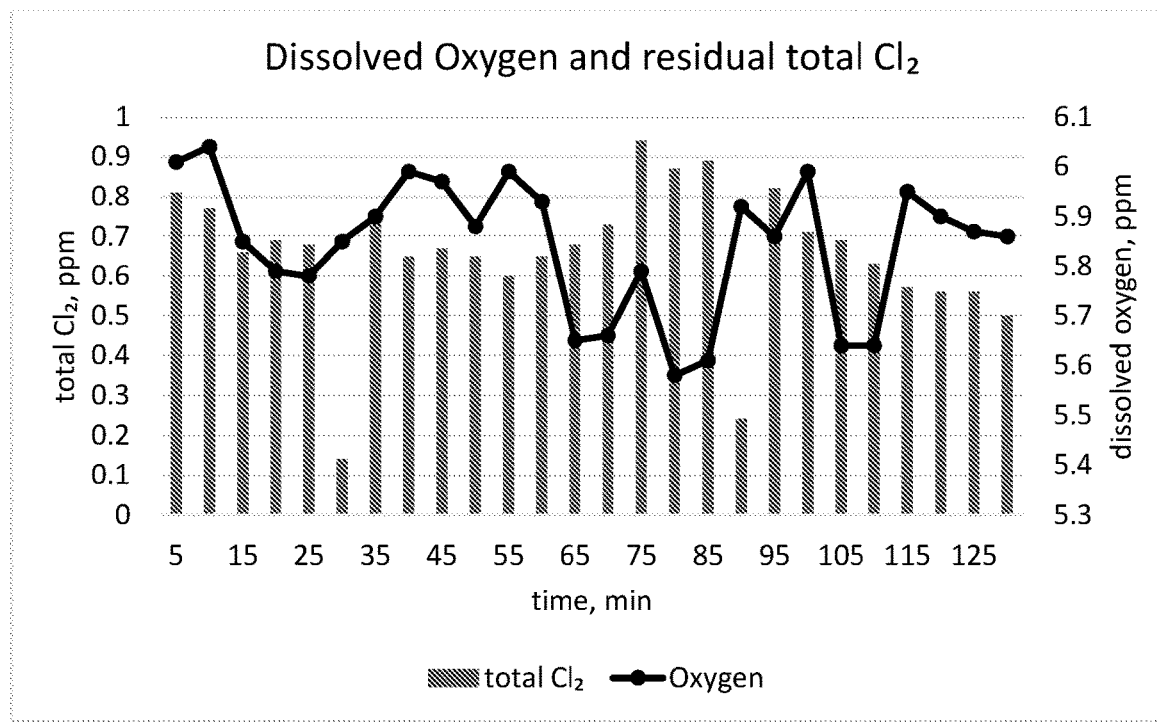
FIG. 13 is a graph showing the levels of dissolved oxygen and total chlorine in process water as a function of time.

On a separate occasion, process water was allowed to stand overnight to allow for microbial growth and diminishing the dissolved oxygen level. Even at these lower levels of dissolved oxygen, the drop in dissolved oxygen when the chlorine residual is high can be observed and shown in FIG. 13.

Example 6

Figure 14:
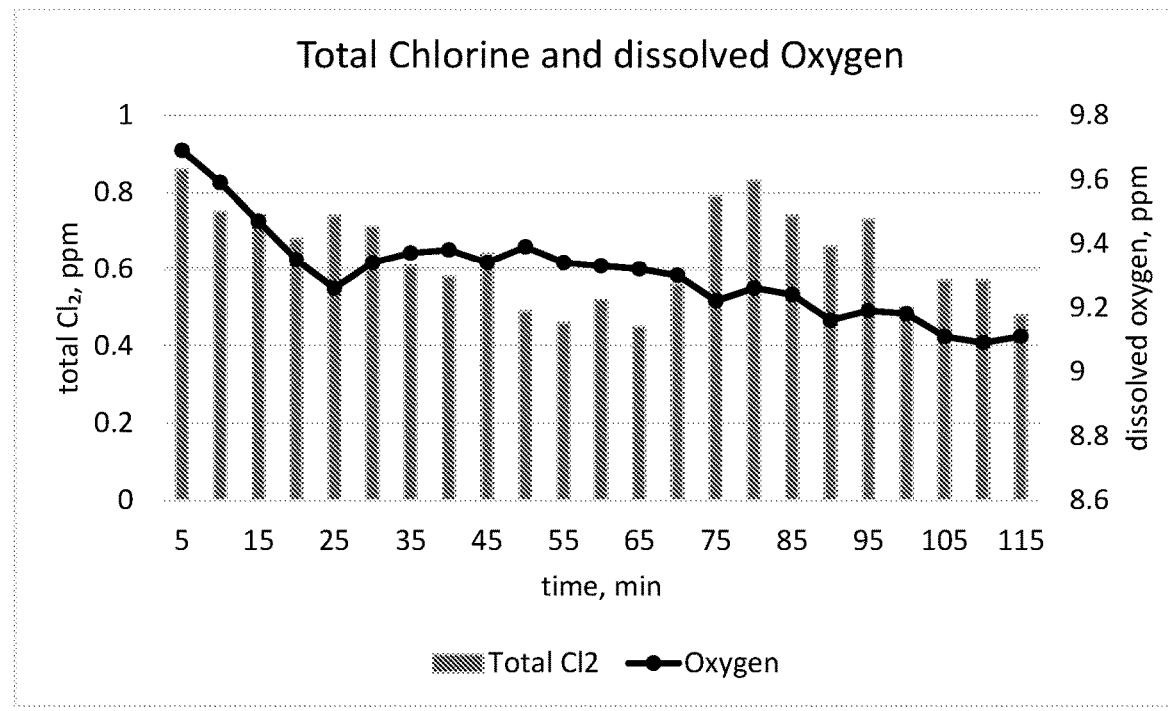
FIG. 14 is a graph showing the levels of dissolved oxygen and total chlorine in process water as a function of time.

Cooling tower water was treated with NAC, a biocide produced by on-site mixing of ammonium carbamate and sodium hypochlorite. NAC was fed to the cooling water every 60 minutes for 4 minutes. Dissolved oxygen was measured online at the cooling tower basin and the residual total chlorine was also measured by an online total chlorine measuring instrument. The initial dissolved oxygen level was high, indicating no problems. The dissolved oxygen dropped, with a minimum in dissolved oxygen during biocide feeding, a slight increase and stabilization of dissolved oxygen while residual total chlorine was stable, and an additional reduction in dissolved oxygen while the residual total chlorine increased during the following feeding of NAC. The results are shown in FIG. 14.

The drop in dissolved oxygen when the residual chlorine is highest indicates a fault in the biocide production or degradation of the biocide upon mixing with the process water and can continue if steps to resolve the problem are not taken. An adsorbable organic halogens (AOX) analysis was conducted at the same time and confirmed that the AOX was 0.18 ppm instead of the regular expected value of 0.014 ppm. These findings correlate the drop in dissolved oxygen during biocide feeding with production of a mixture of chloramines rather than production of monochloramine alone due to lack of balance between sodium hypochlorite and ammonium carbamate. The corrective step to be taken would be to lower the ratio between the feed rate of hypochlorite and the feed rate of ammonium carbamate.

Example 7

Figure 15:
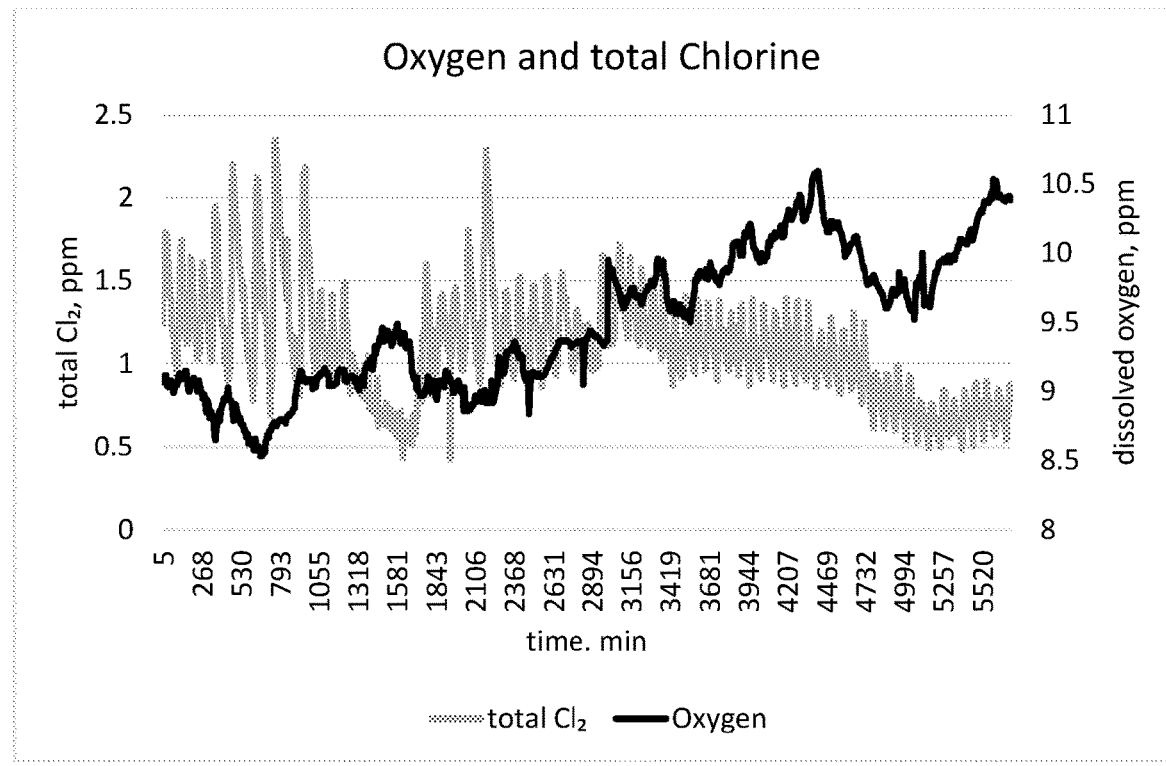
FIG. 15 is a graph showing the levels of dissolved oxygen and total chlorine in process water as a function of time.
Figure 16:
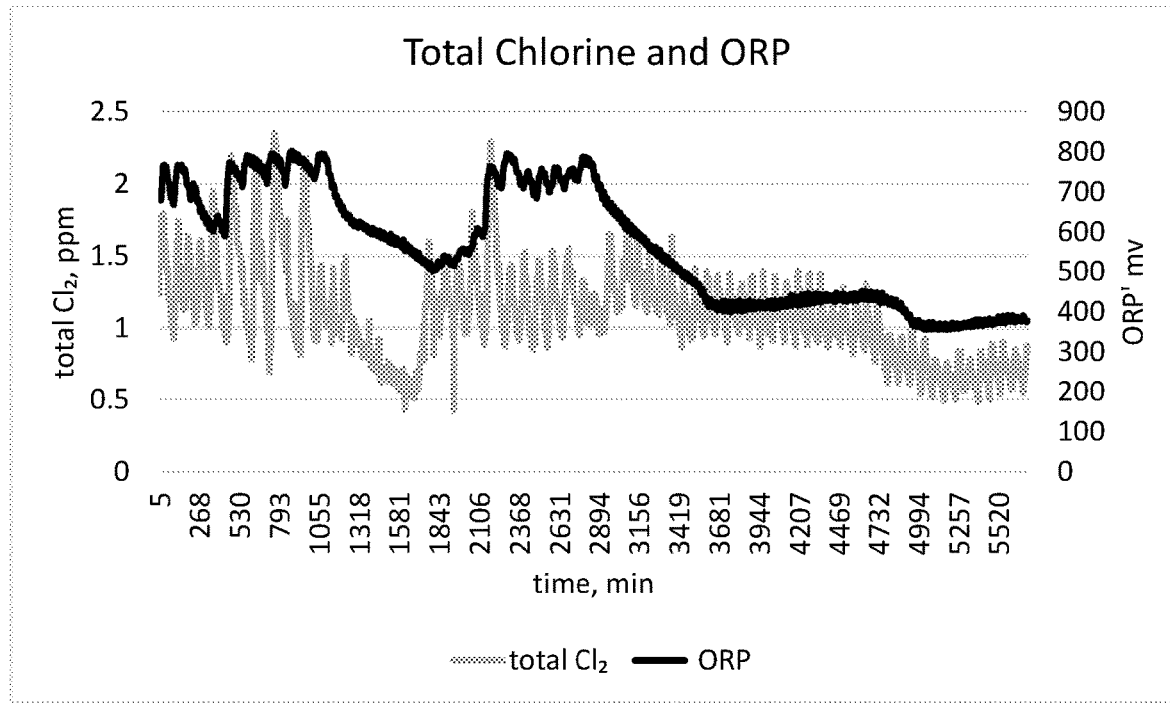
FIG. 16 is a graph showing the level of total chlorine and the oxidation-reduction potential in process water as a function of time.

Cooling tower water was treated with NAC, a biocide produced by on-site mixing of ammonium carbamate and sodium hypochlorite. Residual total chlorine and dissolved oxygen were monitored. A decrease in dissolved oxygen was observed whenever the residual total chlorine increased as shown in FIG. 15, showing a fault in the production of the biocide. Investigation of the fault revealed that the ammonium carbamate container was almost empty and what was being fed to the cooling water was mainly sodium hypochlorite. Sodium hypochlorite is a strong oxidizer which quickly degrades with consumption of oxygen. A high concentration of sodium hypochlorite creates polychlorinated amines and other undesirable disinfection by-products. ORP measurements confirmed that what was being fed to the system was a strong oxidizer as shown in FIG. 16.

Figure 17:
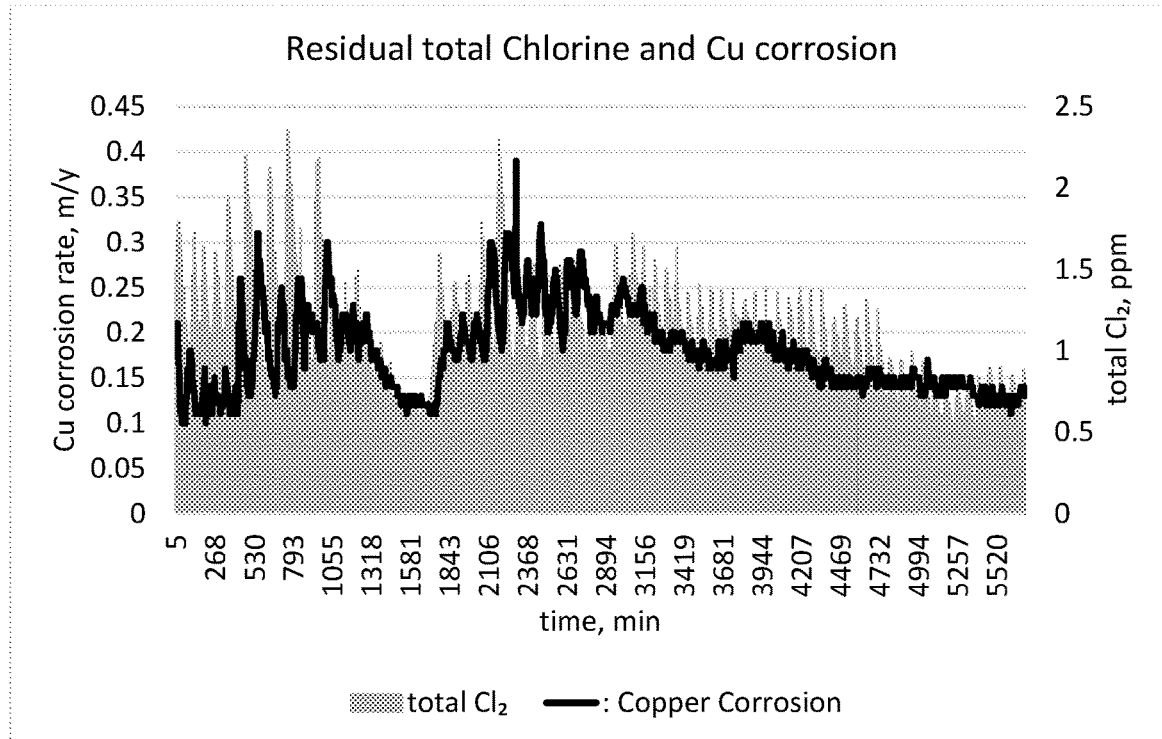
FIG. 17 is a graph showing the level of total chlorine and the rate of copper corrosion in process water as a function of time.
Figure 18:
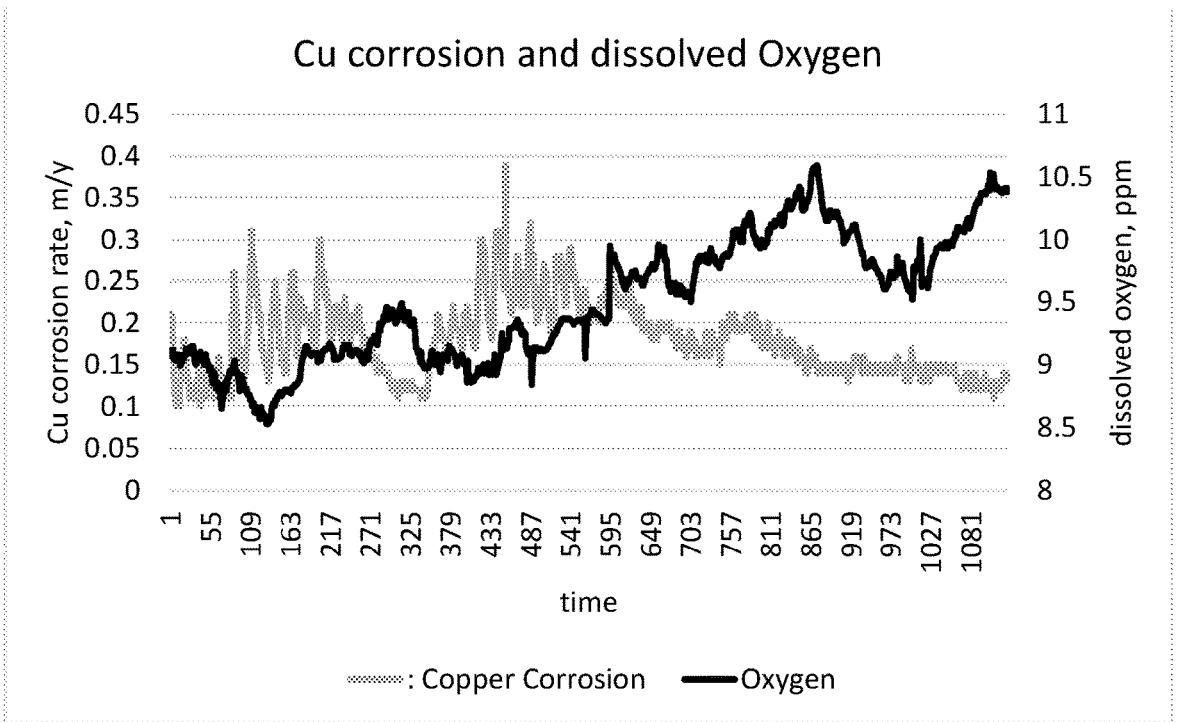
FIG. 18 is a graph showing the level of dissolved oxygen and the rate of copper corrosion in process water as a function of time.

The cooling tower is protected from copper corrosion by adding tolyltriazole to the cooling water as a copper corrosion inhibitor. The corrosion inhibitor does not react with monochloramine but it does react with strong oxidizers such as sodium hypochlorite, reducing the copper corrosion inhibition. Copper corrosion was measured and the copper corrosion rate was found to correlate with the residual chlorine as shown in FIG. 17. FIG. 18 shows that the dissolved oxygen decreased as corrosion increased and vice versa. This demonstrates that dissolved oxygen can be an indicator for corrosion as well as for faulty biocide feeding with its potential production of disinfection by-products.

Example 8

An oxygen electrode was installed in process water of a paper machine using recycled fiber. The paper machine used NAC as its biocide, and the feeding was intermittent at several feeding points along the machine. The electrode measured dissolved oxygen continuously for two months. In parallel, the operators measured process water parameters once a day on weekdays, sampling various points in the process water. Samples were taken at random times, during biocide feeding and during biocide off feeding time. The parameters monitored were: pH, ORP, conductivity, ATP, residual chlorine and dissolved oxygen. Lab measurements of dissolved oxygen were based on the equipment standard procedure: the electrode was placed in the sample, and dissipation of oxygen was followed until the consumption of oxygen ended and the reading of residual dissolved oxygen (%) was stable. The online oxygen electrode measured % dissolved oxygen every minute, and the data presented in this example was limited to data points collected during NAC feeding to the same feeding line.

Figure 19:
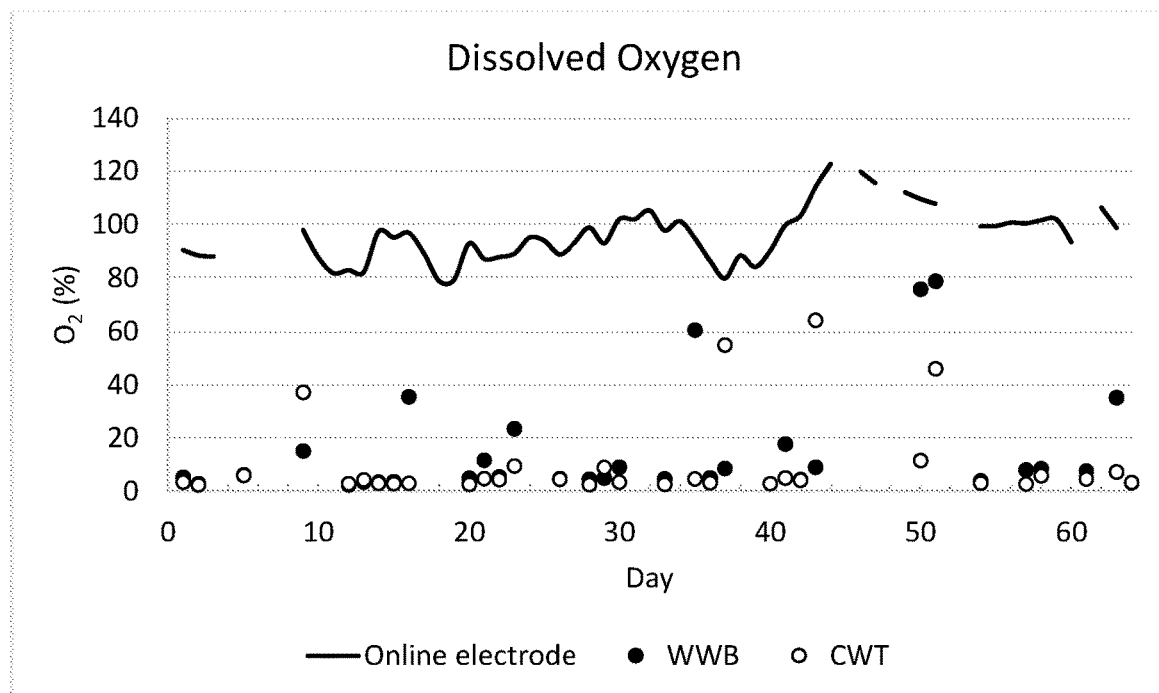
FIG. 19 is a graph showing the level of dissolved oxygen in process water as a function of time.
Figure 20:
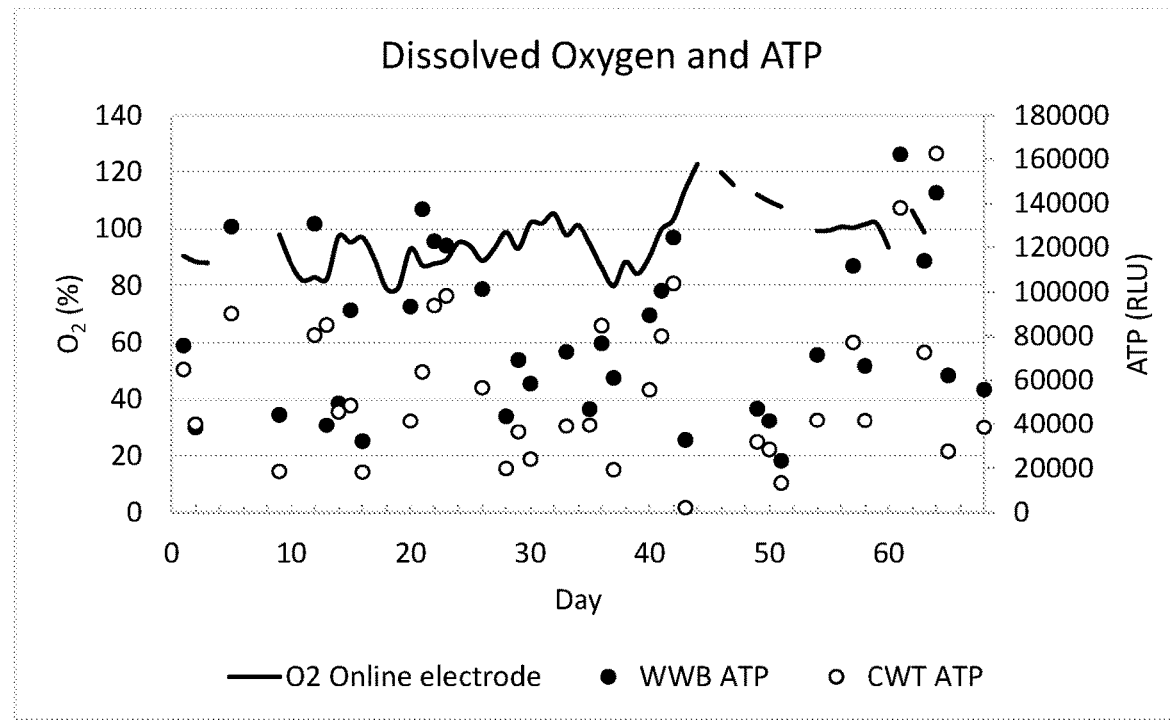
FIG. 20 is a graph showing the levels of dissolved oxygen and adenosinde triphosphate (ATP) in process water as a function of time.

A daily average of the online oxygen measurements and lab measurements at two sampling points are presented in FIG. 19. The lab measurements were taken at the WWB: white water bottom, one of the machine NAC feeding points, the closest feeding point to the online electrode, and CWT: clear water tower, the next big water chest close to the oxygen electrode. FIG. 19 clearly shows that the online electrode measured consistently high values of $O_2$% from 80% to 120%, yet there were clear differences in the daily average oxygen saturation results. The lab samples showed higher residual dissolved oxygen in some samples, but usually the level of dissolved oxygen was very low. FIG. 20 presents adenosine triphosphate (ATP) measurement results. ATP is produced by bacteria and indicates bacterial activity. The values were mostly high, indicating high contamination of the paper process water. The online oxygen results measured continuously and without enabling the electrode to get to a stable reading show much higher values, and thus it was shown that the results of the daily average of the online electrode reading cannot be used to monitor on line process water microbial contamination, as is supported also by the prior art.

Figure 21:
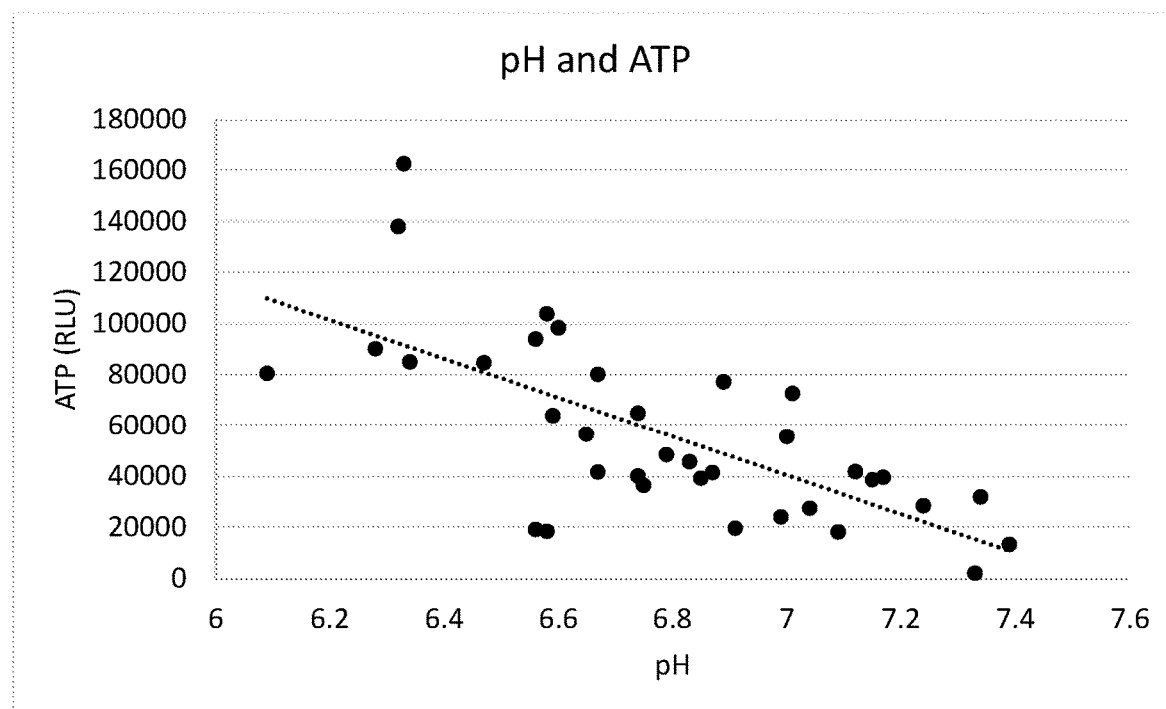
FIG. 21 is a graph showing the level of ATP in process water as a function of the pH.
Figure 22:
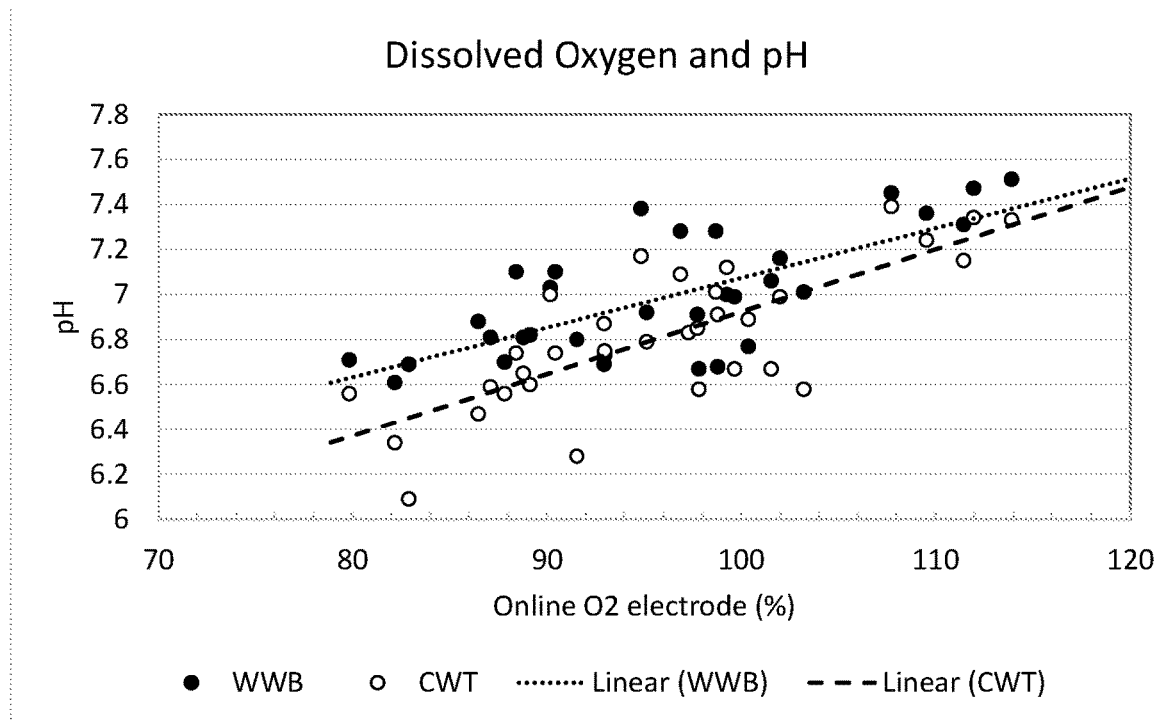
FIG. 22 is a graph showing the pH in process water as a function of the level of dissolved oxygen.

FIG. 21 shows a clear correlation between ATP and pH in the lab samples. This correlation is not surprising since bacteria in process water produce acids as starch is degraded. The amount of acid produced is related to the amount of microbial activity. The results in FIG. 22 show a clear correlation between process water lab tested pH values and online daily average values of dissolved oxygen. This finding shows that even though the online oxygen electrode average results cannot be directly correlated with the biological activity in the process water and the actual values measured online do not reflect the real decay of oxygen due to microbial consumption, the average dissolved oxygen values can be used to assess the level of microbial contamination in the process water.

Figure 23:
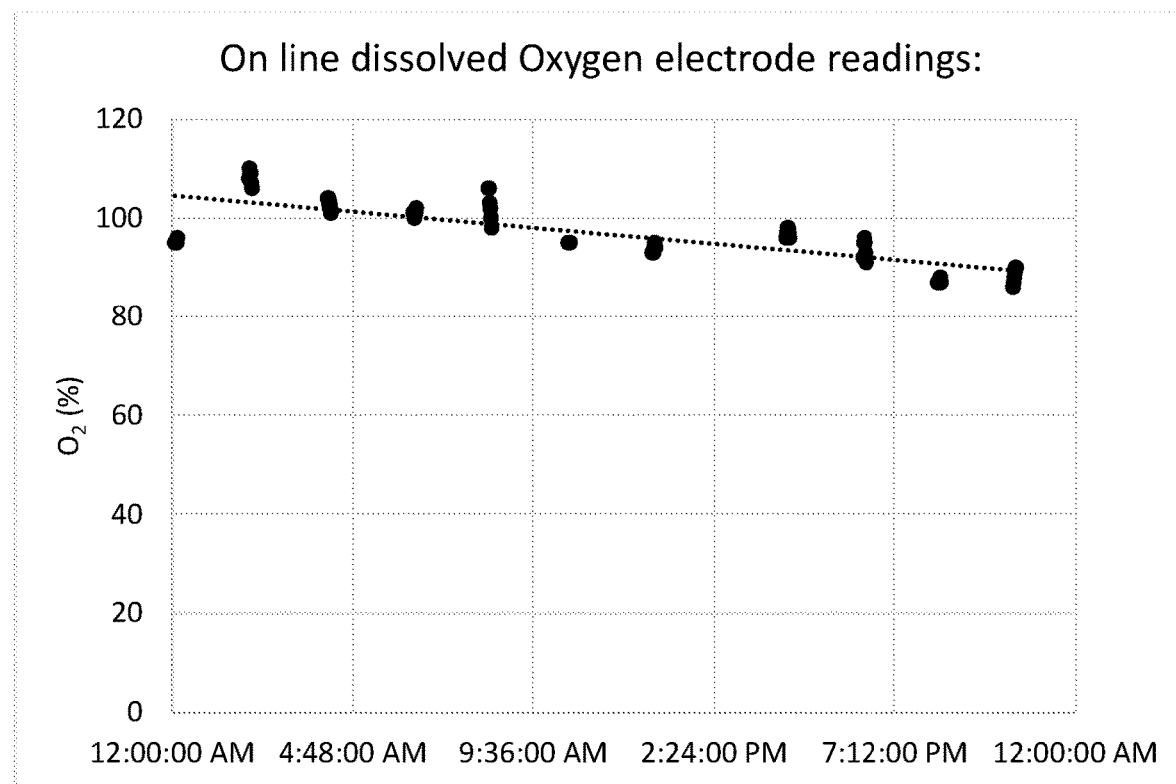
FIG. 23 is a graph showing the level of dissolved oxygen in process water as a function of time.

FIG. 23 shows the actual readings of an online oxygen electrode during NAC feeding to one feeding point for a 24 hour period. The online oxygen readings steadily decrease and clearly demonstrate loss of control and increase in growth of microorganisms. This shows that continuous online monitoring is effective in detecting loss of biological control in process water. Such online data can be used for automatic corrective steps to prevent further deterioration.

It will be appreciated by persons skilled in the art that the present invention is not limited to what has been particularly shown and described hereinabove. Rather the scope of the present invention includes both combinations and subcombinations of various features described hereinabove as well as modifications thereof which would occur to a person of skill in the art upon reading the foregoing description and which are not in the prior art.

The invention claimed is:

1. A system for feeding an oxidizing biocide to process water being treated with said biocide and monitoring said process water for potential degradation of said biocide thereby forming, as a result of such degradation, an active halogen compound, the system comprising:
    a biocide production system for forming said biocide;
    a biocide feeding conduit for feeding said biocide to said process water being treated with said biocide at a biocide inlet; and
    a degradation detection module including a dissolved oxygen sensor downstream of said biocide inlet;
    wherein said dissolved oxygen sensor is situated such that the time for said process water to flow from said biocide inlet to said dissolved oxygen sensor is not more than 30 minutes; and
    wherein said biocide is not formed in said process water.

2. The system according to claim 1, wherein said biocide production system produces said oxidizing biocide synchronously with said feeding by mixing a hypochlorite oxidant and an ammonium salt.

3. The system according to claim 1, wherein said dissolved oxygen sensor is a luminescence based dissolved oxygen sensor.

4. The system according to claim 1, further comprising a controller that records measurements of said dissolved oxygen sensor.

5. The system according to claim 4, wherein said controller includes a display to display a warning based on the measurements of said dissolved oxygen sensor.

6. The system according to claim 4, wherein said controller includes a functionality for sending a warning to a remote location.

7. The system according to claim 4, wherein said controller, when operating in a background mode, generates a baseline value for a dissolved oxygen level.

8. The system according to claim 7, wherein said controller raises a warning if the dissolved oxygen level deviates from the baseline value more than a preset threshold.

9. The system according to claim 4, wherein said controller, when operating in a feeding mode, raises a warning if there is a decrease in a dissolved oxygen level during feeding of the biocide or during an extended measurement period immediately following the feeding of said biocide.

10. The system according to claim 4, wherein said controller is in communication with a biocide production system for producing said oxidizing biocide synchronously with said feeding, wherein said controller has functionality to control said biocide production system.

11. The system according to claim 1, wherein the time for said process water to flow from said biocide inlet to said dissolved oxygen sensor is not more than 20 minutes.

12. The system according to claim 1, wherein said active halogen compound is selected from the group consisting of HOCl, HOBr, $NHCl_2$ and $NH_2Br$.

13. The system according to claim 1, wherein said dissolved oxygen sensor is located in the flow of said process water.

14. A method for monitoring potential degradation of an oxidizing biocide in a process of forming said oxidizing biocide and feeding said oxidizing biocide to process water being treated by said biocide, thereby forming, as a result of such degradation, an active halogen compound, the method comprising:
- providing a dissolved oxygen sensor in said process water being treated by said biocide downstream from a biocide inlet; and
- employing said dissolved oxygen sensor for periodically measuring a level of dissolved oxygen in said process water;
- wherein the time for said process water to flow from said biocide inlet to said dissolved oxygen sensor is not more than 30 minutes; and
- wherein said biocide is not formed in said process water.

15. The method according to claim 14, wherein forming said oxidizing biocide comprises producing said oxidizing biocide synchronously with feeding said oxidizing biocide to said process water, wherein said producing comprises producing said oxidizing biocide by mixing a hypochlorite oxidant and an ammonium salt.

16. The method according to claim 14, wherein said dissolved oxygen sensor is a luminescence based dissolved oxygen sensor.

17. The method according to claim 14, further comprising communicating the level of dissolved oxygen to a controller.

18. The method according to claim 17, wherein said controller includes a display to display a warning based on measurements of the dissolved oxygen sensor.

19. The method according to claim 17, wherein said controller includes a functionality for sending a warning to a remote location.

20. The method according to claim 17, wherein said controller, when operating in a background mode, generates a baseline value for the dissolved oxygen level.

21. The method according to claim 20, wherein said controller raises a warning if the dissolved oxygen level deviates from the baseline value more than a preset threshold.

22. The method according to claim 17, wherein said controller, when operating in a feeding mode, raises a warning if there is a decrease in the dissolved oxygen level during said feeding or during an extended measurement period following said feeding.

23. The method according to claim 17, wherein said controller is in communication with a biocide production system for producing said oxidizing biocide synchronously with said feeding, wherein said controller has functionality to control said biocide production system.

24. The method according to claim 14, wherein the time for said process water to flow from said biocide inlet to said dissolved oxygen sensor is not more than 20 minutes.

25. The method according to claim 14, wherein said active halogen compound is selected from the group consisting of $HOCl$, $HOBr$, $NHCl_2$ and $NH_2Br$.

26. The method according to claim 14, wherein said dissolved oxygen sensor is located in the flow of said process water.

* * * * *